United States Patent
Qiu et al.

(10) Patent No.: US 12,169,199 B2
(45) Date of Patent: Dec. 17, 2024

(54) ACTIVITY BASED HOST CELL PROTEIN PROFILING

(71) Applicant: Regeneron Pharmaceuticals, Inc., Tarrytown, NY (US)

(72) Inventors: Haibo Qiu, Hartsdale, NY (US); Rosalynn Molden, Shoreline, WA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 627 days.

(21) Appl. No.: 17/187,778

(22) Filed: Feb. 27, 2021

(65) Prior Publication Data

US 2021/0270824 A1 Sep. 2, 2021

Related U.S. Application Data

(60) Provisional application No. 63/073,125, filed on Sep. 1, 2020, provisional application No. 63/021,181, filed on May 7, 2020, provisional application No. 62/982,346, filed on Feb. 27, 2020.

(51) Int. Cl.
| | | |
|---|---|---|
| *G01N 33/543* | (2006.01) | |
| *A61K 38/46* | (2006.01) | |
| *A61K 47/26* | (2006.01) | |
| *G01N 21/64* | (2006.01) | |
| *G01N 30/72* | (2006.01) | |
| *G01N 33/68* | (2006.01) | |

(52) U.S. Cl.
CPC ..... *G01N 33/54306* (2013.01); *A61K 38/465* (2013.01); *A61K 47/26* (2013.01); *G01N 21/6428* (2013.01); *G01N 30/7233* (2013.01); *G01N 30/7266* (2013.01); *G01N 33/6848* (2013.01); *C12Y 301/01001* (2013.01)

(58) Field of Classification Search
CPC ......... G01N 33/54306; G01N 21/6428; G01N 30/7233; G01N 30/7266; G01N 33/6848; A61K 38/465; A61K 47/26
See application file for complete search history.

(56) References Cited

FOREIGN PATENT DOCUMENTS

WO WO-2018039499 A1 * 3/2018 ............. C07K 16/00

OTHER PUBLICATIONS

Kidd, Dana, Yongsheng Liu, and Benjamin F. Cravatt. "Profiling serine hydrolase activities in complex proteomes." Biochemistry 40.13 (2001): 4005-4015. (Year: 2001).*

Hirsch, James D., et al. "Easily reversible desthiobiotin binding to streptavidin, avidin, and other biotin-binding proteins: uses for protein labeling, detection, and isolation." Analytical biochemistry 308.2 (2002): 343-357. (Year: 2002).*

(Continued)

*Primary Examiner* — Louise W Humphrey
*Assistant Examiner* — Candice Lee Swift
(74) *Attorney, Agent, or Firm* — Kramer Levin Naftalis & Frankel LLP

(57) ABSTRACT

The present application provides methods and systems for identifying host cell protein impurities which have enzymatic activities in biopharmaceutical products and in samples during manufacturing processes. The present application provides various activity-based probes to characterize different enzyme classes of host cell protein impurities including probes containing functionalized molecules with reporter or affinity-based tags.

29 Claims, 12 Drawing Sheets

(56) References Cited

OTHER PUBLICATIONS

Simon, Gabriel M., and Benjamin F. Cravatt. "Activity-based proteomics of enzyme superfamilies: serine hydrolases as a case study." Journal of Biological Chemistry 285.15 (2010): 11051-11055. (Year: 2010).*

Thermo Fisher; https://www.thermofisher.com/us/en/home/life-science/protein-biology/protein-biology-learning-center/protein-biology-resource-library/protein-biology-application-notes/serine-hydrolase-active-site-probes.html; accessed Aug. 16, 2023 (Year: 2011).*

Liu, Xinrong, et al. "Identification and characterization of co-purifying CHO host cell proteins in monoclonal antibody purification process." Journal of Pharmaceutical and Biomedical Analysis 174 (2019): 500-508. (Year: 2019).*

Li Xuanwen et al: "Profiling Active Enzymes for Polysorbate Degradation in Biotherapeutics by Activity-Based Protein Profiling," bioRxiv, Oct. 8, 2020 (Oct. 8, 2020), pp. 1-34.

Zhang Sisi et al: "Rapid Polysorbate 80 Degradation by Liver Carboxylesterase in a Monoclonal Antibody Formulated Drug Substance at Early Stage Development," Journal of Pharmaceutical Sciences, vol. 109, No. 11, Nov. 1, 2020 (Nov. 1, 2020), pp. 3300-3307.

Li Xuanwen et al: "Profiling Active Enzymes for Polysorbate Degradation in Biotherapeutics by Activity-Based Protein Profiling," Analytical Chemistry, May 25, 2021 (May 25, 2021), pp. 1-9.

I-Hsuan Chen et al: "Improved Host Cell Protein Analysis in Monoclonal Antibody Products through Molecular Weight Cutoff Enrichment," Analytical Chemistry, vol. 92, No. 5, Jan. 30, 2020 (Jan. 30, 2020), pp. 3751-3757.

Yang Pengyu et al: "Activity-Based Protein Profiling: Recent Advances in Probe Development and Applications," Chembiochem, vol. 16, No. 5, Feb. 4, 2015 (Feb. 4, 2015), pp. 712-724.

Jenny Heidbrink Thompson et al: "Improved detection of host cell proteins (HCPs) in a mammalian cell-derived antibody drug using liquid chromatography/mass spectrometry in conjunction with an HCP-enrichment strategy : LC/MS for host cell protein analysis," Rapid Communications in Mass Spectrometry, vol. 28, No. 8, Mar. 5, 2014 (Mar. 5, 2014), pp. 855-860.

Fonovic Marko et al: "Activity-based probes as a tool for functional proteomic analysis of proteases," Expert Review of Proteomics, Future Drugs Ltd., London, GB, vol. 5, No. 5, Oct. 1, 2008 (Oct. 1, 2008), pp. 721-730.

International Search Report, PCT Application No. PCT/US2021/020136, Application Filing Date Feb. 27, 2021, Date of Mailing Jun. 22, 2021.

Cardoza et al "Mass Spectrometry-based Proteomics: Qualitative Identification to Activity-based Protein Profiling" Wiley Interdiscip Rev Syst Biol Med. Mar. 2012; 4(2): 141-162.

\* cited by examiner

ACTIVITY BASED HOST CELL PROTEIN PROFILING

CROSS-REFERENCE TO RELATED APPLICATIONS

This application claims priority to U.S. Provisional Patent Application No. 63/073,125, filed Sep. 1, 2020, U.S. Provisional Patent Application No. 62/982,346, filed Feb. 27, 2020 and U.S. Provisional Patent Application No. 63/021,181, filed May 7, 2020, the contents of which are incorporated herein by reference in their entirety.

FIELD

The present invention generally pertains to methods and systems for identifying host cell protein impurities which have enzymatic activities. These methods and systems can be applied in biopharmaceutical products and in samples during manufacturing processes to identify and monitor the host cell protein impurities.

BACKGROUND

During manufacturing of biopharmaceutical products, such as the purification of monoclonal antibodies, it is required to remove impurities to obtain biopharmaceutical products having high purities. In particular, since DNA technology has been used widely for producing biopharmaceutical products in host cells, residual host cell proteins (HCPs) can present potential safety risks to patients due to compromised product quality and stability. For producing recombinant therapeutic antibodies, several purification processes are needed to ensure that the antibody product is highly purified. Any residual impurities after conducting the bioprocesses should be present at an acceptable low level prior to conducting clinical studies. In particular, HCPs derived from mammalian expression systems, for example, Chinese hamster ovary (CHO) cells, should be monitored and controlled in the final drug substance. Sometimes, trace amounts of particular HCPs may cause an immune response or toxic biologic activities after drug injection, even though the total HCPs may be present at very low levels. Therefore, there are unmet needs to identify and monitor specific HCPs for risk assessment.

The presence of residual HCPs can cause potential safety risks or problems in drug stability, especially HCPs which have enzymatic activities, such as active proteases. It will be appreciated that a need exists for methods and systems to identify, profile, characterize, and quantify HCP impurities which have enzymatic activities. These methods and systems should provide robust, reliable and sensitive detection of enzymatic HCP impurities in biopharmaceutical products and in samples during manufacturing processes.

SUMMARY

Defining acceptable levels of host cell protein (HCP) impurities has become a critical issue for using biological systems to manufacture therapeutic products. There are a large number of HCP impurities, for example, potentially thousands of components, which have to be controlled and monitored, to ensure the safety and efficacy of biopharmaceutical products.

The present application provides methods and systems for identifying, profiling, characterizing or quantifying HCP impurities which have enzymatic activities. These methods and systems can be used to identify and monitor the HCP impurities in biopharmaceutical products and in samples during manufacturing processes, including providing various activity-based probes to characterize different enzyme classes of HCP impurities.

This disclosure provides a method of identifying, profiling, characterizing or quantifying HCP impurities in a sample. In some exemplary embodiments, the method of the present application comprises contacting the sample with at least one probe to provide probe-attached HCP impurities, wherein the probe comprises a warhead and a tag, wherein the warhead is capable of binding to an active site of the probe-attached HCP impurity, and wherein the sample comprises at least one high-abundance protein. In one aspect, the warhead of the probe of the method is capable of binding covalently to a residue in the active site of the probe-attached HCP impurity. In one aspect, the tag of the probe of the method is a conjugation tag, an affinity tag, or a reporter tag.

In one aspect, the method of the present application further comprises: contacting the sample with a solid support, subsequently washing the solid support using a solution to isolate the probe-attached HCP impurities and to provide an eluent, treating the eluent with an enzymatic digestion reaction to generate components of the isolated probe-attached HCP impurities, and subsequently identifying, profiling, characterizing or quantifying the components of the isolated probe-attached HCP impurities using a mass spectrometer; wherein the solid support comprises a ligand, and wherein the ligand is capable of binding to the tag.

In one aspect, the warhead of the probe of the method of the present application comprises an enzymatic inhibitor, an enzymatic substrate-based scaffold or a protein-reactive molecule. In one aspect, the at least one probe of the method of the present application further comprises a linker. In one aspect, the at least one high-abundance protein in the sample of the method is an antibody, a bispecific antibody, an antibody fragment, a Fab region of an antibody, an antibody-drug conjugate, a fusion protein, a protein pharmaceutical product or a drug. In another aspect, an enzyme of the enzymatic digestion reaction of the method is trypsin.

In one aspect, the mass spectrometer of the method of the present application is an electrospray ionization mass spectrometer, nano-electrospray ionization mass spectrometer, such as an Orbitrap mass spectrometer, a Q-TOF mass spectrometer or a triple quadrupole mass spectrometer, wherein the mass spectrometer is coupled to a liquid chromatography system. In one aspect, the mass spectrometer of the method is capable of performing LC-MS (liquid chromatography-mass spectrometry), nano-LC-MS, LC-MS/MS, nano-LC-MS/MS or LC-MRM-MS (liquid chromatography-multiple reaction monitoring-mass spectrometry) analyses.

In one aspect, the tag of the probe of the method is detected using Western blot, capillary electrophoresis, SDS-PAGE, fluorescent visualization, or fluorescent gel imaging. In another aspect, the active site of the probe-attached HCP impurity of the method is a cysteine protease active site, a serine protease active site, a serine hydrolase active site, a cathepsin active site, a metalloprotease active site, a cholinesterase active site, an active site of a lipid-binding protein, an active site of a sphingolipid-binding protein, an active site of a ceramide-binding protein, a lipase active site, a protease active site, a hydrolase active site, an oxidoreductase active site, or an isomerase active site.

In one aspect, the tag of the probe of the method comprises a fluorophore or a fluorophore conjugation site, such as rhodamine, biotin, phosphine, alkyne, azide, acetylene, cyclooctyne, phenyl azide or omega-terminal azide. In one aspect, the warhead of the probe comprises fluorophosphonate, epoxysuccinate, photo-activatable lipid, photo-activatable sphingosine, N-acetylated amino acid, quinolimine methide coupled amino acid, or p-aminomandelic acid coupled amino acid. In one aspect, the probe of the method of the present application comprises azido-fluorophosphonate; desthiobiotin-fluorophosphonate; tetramethylrhodamine-fluorophosphonate; ethyl (2S,3S)-epoxysuccinate-Leu-Tyr-Acp-Lys(Biotin)-NH$_2$; 1-palmitoyl-2-(9-(3-pent-4-ynyl-3-H-diazirin-3-yl)-nonanoyl)-sn-glycero-3-phosphocholine; (2S,3R,E)-2-amino-13-(3-(pent-4-yn-1-yl)-3H-diazirin-3-yl)tridec-4-ene-1,3-diol; N-(9-(3-pent-4-ynyl-3-H-diazirin-3-yl)-nonanoyl)-D-erythro-sphingosine; 1,2-dipalmitoyl-sn-glycero-3-phosphoethanolamine-N-(5-hexynoyl); or D-galactosyl-β-1,1' N-(6"-azidohexanoyl)-D-erythro-sphingosine.

This disclosure, at least in part, provides a system for identifying, profiling, characterizing or quantifying HCP impurities in a sample. In some exemplary embodiments, the system of the present application comprises: at least one probe, wherein the at least one probe comprises a warhead and a tag, wherein the at least one probe is capable of binding to HCP impurities to provide probe-attached HCP impurities, wherein the warhead is capable of binding to an active site of the probe-attached HCP impurity, and wherein the sample comprises at least one high-abundance protein; a solid support, wherein the solid support comprises a ligand which is capable of binding to the tag; a solution for washing the solid support to isolate the probe-attached HCP impurities and to provide an eluent; an enzymatic digestion solution capable of generating components of the isolated probe-attached HCP impurities; and a mass spectrometer capable of identifying, profiling, characterizing and/or quantifying the components from the isolated probe-attached HCP impurity.

In one aspect, the warhead of the probe of the system is capable of binding covalently to a residue in the active site of the probe-attached HCP impurity. In one aspect, the tag of the probe of the system is a conjugation tag, an affinity tag or a reporter tag. In another aspect, the warhead of the probe of the system comprises an enzymatic inhibitor, an enzymatic substrate-based scaffold or a protein-reactive molecule. In another aspect, the at least one probe of the system further comprises a linker. In yet another aspect, the at least one high-abundance protein in the sample of the system is an antibody, a bispecific antibody, an antibody fragment, a Fab region of an antibody, an antibody-drug conjugate, a fusion protein, a protein pharmaceutical product or a drug. In one aspect, an enzyme of the enzymatic digestion solution of the system is trypsin.

In one aspect, the mass spectrometer of the system is an electrospray ionization mass spectrometer, nano-electrospray ionization mass spectrometer, such as an Orbitrap mass spectrometer, a Q-TOF mass spectrometer or a triple quadrupole mass spectrometer, wherein the mass spectrometer is coupled to a liquid chromatography system. In another aspect, the mass spectrometer of the system is capable of performing LC-MS (liquid chromatography-mass spectrometry), nano-LC-MS, LC-MS/MS, nano-LC-MS/MS or a LC-MRM-MS (liquid chromatography-multiple reaction monitoring-mass spectrometry) analyses. In one aspect, the tag of the probe of the system is detected using Western blot, capillary electrophoresis, SDS-PAGE, fluorescent visualization, or fluorescent gel imaging.

In one aspect, the active site of the probe-attached HCP impurity is a cysteine protease active site, a serine protease active site, a serine hydrolase active site, a cathepsin active site, a metalloprotease active site, a cholinesterase active site, an active site of a lipid-binding protein, an active site of a sphingolipid-binding protein, an active site of a ceramide-binding protein, a lipase active site, a protease active site, a hydrolase active site, an oxidoreductase active site, or an isomerase active site. In one aspect, the tag of the probe of the system comprises a fluorophore or a fluorophore conjugation site, such as rhodamine, biotin, phosphine, alkyne, azide, acetylene, cyclooctyne, phenyl azide, or omega-terminal azide.

In one aspect, the warhead of the probe of the system comprises fluorophosphonate, epoxysuccinate, photo-activatable lipid, photo-activatable sphingosine, N-acetylated amino acid, quinolimine methide coupled amino acid, or p-aminomandelic acid coupled amino acid. In one aspect, the probe of the system comprises azido-fluorophosphonate; desthiobiotin-fluorophosphonate; tetramethylrhodamine-fluorophosphonate; ethyl (2S,3S)-epoxysuccinate-Leu-Tyr-Acp-Lys(Biotin)-NH$_2$; 1-palmitoyl-2-(9-(3-pent-4-ynyl-3-H-diazirin-3-yl)-nonanoyl)-sn-glycero-3-phosphocholine; (2S,3R,E)-2-amino-13-(3-(pent-4-yn-1-yl)-3H-diazirin-3-yl)tridec-4-ene-1,3-diol; N-(9-(3-pent-4-ynyl-3-H-diazirin-3-yl)-nonanoyl)-D-erythro-sphingosine; 1,2-dipalmitoyl-sn-glycero-3-phosphoethanolamine-N-(5-hexynoyl); or D-galactosyl-β-1,1' N-(6"-azidohexanoyl)-D-erythro-sphingosine.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

DETAILED DESCRIPTION

Figure 1:
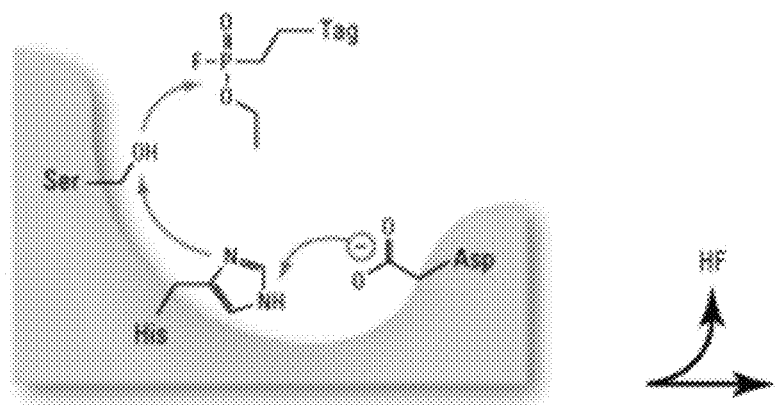
FIG. 1 shows a probe containing a tag and a fluorophosphonate (FP) group which is capable of covalently and specifically attaching to a serine residue in the active site of serine hydrolases, including lipases and proteases, according to an exemplary embodiment.
Figure 1:
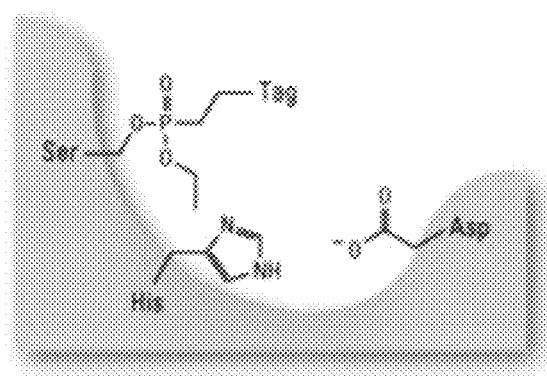

The presence of host cell protein (HCP) impurities in biopharmaceutical products can impact some clinical consequences including drug efficacy and patient safety. Various approaches have been used to detect and identify HCP impurities in biopharmaceutical products and in samples from manufacturing steps. Some HCP impurities have enzymatic activities, for example, enzymatic HCP impurities. The identification of specific HCPs which have enzymatic activities can provide important information to assess the risk of HCPs to product safety.

The present application provides methods and systems to characterize, profile, identify or quantify HCP impurities which have enzymatic activities, for example, activity-based HCP profiling, including uses of activity-based probes. The present application provides various activity-based probes to characterize different enzyme classes. The activity-based probes of the present application include functionalized small-molecules and a tag, such as a reporter tag or an affinity-based tag, to directly monitor the enzyme activity of a given target or sets of targets. Some activity-based probes of the present application can covalently bind to enzymatic active sites for profiling different classes of enzymes based on the specific catalytic mechanisms. For example, specific lipids having affinities to lipases can be used as activity-based probes to enrich HCP impurities which have lipase activities. Similar approaches can be used for characterizing, profiling, identifying or quantifying serine hydrolases, cathepsins, lipid binding proteins, and metalloproteases.

Activity-based protein profiling has been used to investigate the changes of catalytic activity of enzyme classes in complex proteome, rather than quantitating the protein abundance. Activity-based protein profiling can be used to functionally annotate the enzyme function of proteins. Different probes have been used to differentially label active proteins including proteases, hydrolases, oxidoreductases and isomerases (Blais et al., Activity-based proteome profiling of hepatoma cells during Hepatitis C virus replication using protease substrate probes, Journal of Proteome Research, 2010 Feb. 5;9(2):912-23. doi: 10.1021/pr900788a). Blais et al. utilized a group of probes composed of an N-acetylated amino acid, which mimics the $P_1$ position in protease peptide substrates bearing distinct amino acids, such as serine, threonine, phenylalanine, glutamic acid and histidine. The activity-based probes can include amino acid coupled quinolimine methide probes and amino acid coupled p-aminomandelic acid probes. Activity-based protein profiling also has been used to monitor the functional status of enzymes by utilizing active site-directed probes, such as detecting and analyzing functional annotation of host cell serine hydrolases for host-virus interaction (Shahiduzzaman et al., Activity based protein profiling to detect serine hydrolase alterations in virus infected cells, Frontiers in Microbiology, Aug. 22, 2012, volume 3, article 308, p 1-5). In addition, since activity-based probes can specifically recognize active proteases, they can be used to detect and quantitate proteolytic activity in situ, especially in conjunction with positron emission tomography (Ulrich auf dem Keller et al., Proteomic techniques and activity-based probes for the system-wide study of proteolysis, Biochimie, 92 (2010), page 1705-1714).

In some exemplary embodiments, the present application provides a method of identifying, profiling, characterizing or quantifying HCP impurities in a sample, the method comprising: contacting the sample with at least one probe to provide probe-attached HCP impurities, wherein the probe comprises a warhead and a tag, wherein the warhead is capable of binding to an active site of the probe-attached HCP impurity, and wherein the sample comprises at least one high-abundance protein. In some aspects, the present application provides a system for identifying, profiling, characterizing or quantifying HCP impurities in a sample, the system comprising: at least one probe, wherein the at least one probe comprises a warhead and a tag, wherein the at least one probe is capable of binding to HCP impurities to provide probe-attached HCP impurities, wherein the warhead is capable of binding to an active site of the probe-attached HCP impurity, and wherein the sample comprises at least one high-abundance protein; a solid support, wherein the solid support comprises a ligand which is capable of binding to the tag; a solution for washing the solid support to isolate the probe-attached HCP impurities and to provide an eluent; an enzymatic digestion solution capable of generating components of the isolated probe-attached HCP impurities; and a mass spectrometer capable of identifying, profiling, characterizing or quantifying the components from the isolated probe-attached HCP impurity.

In one aspect, the activity-based probe of the present application is an enzymatic active site-directed probe comprising a warhead, such as a reactive group for reacting and binding to enzymatic active sites. In one aspect, the activity-based probe of the present application comprises a warhead and a tag, such as a reporter tag. In another aspect, the activity-based probe of the present application comprises a warhead, a tag and a linker. In another aspect, the warhead is a reactive group which can bind to or covalently label the active site of an enzyme. In yet another aspect, the warhead is a reactive group, such as a small molecule inhibitor, a substrate-based scaffold or a protein-reactive molecule. In one aspect, the warhead has been designed to target cysteine or serine proteases by covalently binding to the active site residue. Since proteins in the same enzymatic family have similar functions, the active sites of these proteins commonly have similar structures, therefore an active site-directed probe can be reactive to the active sites of many members of a given enzymatic family. In one aspect, the tag is a reporter tag for detection and identification of the labelled enzyme, such as direct molecular imaging or radio-labeling. For example, the tag can be a fluorophore, such as rhodamine, for visualization. In one aspect, the tag is an affinity tag for enrichment or purification, such as biotin. In another aspect, the tag is a labelling tag, such as azides or acetylenes, for in vivo or in situ labeling of proteins. In another aspect, the linker serves as a connector for connecting the warhead and the tag. In one aspect, the linker serves as a spacer between the warhead and the tag including a flexible chain with various length and hydrophobicity. In some aspects, the activity-based probes of the present application are active site-directed probes that consist of small molecule inhibitors linked to reporter tags.

In some exemplary embodiments, serine hydrolase probes are used to label, assay, purify or detect enzymatic HCP impurities which have serine hydrolase activities. Serine hydrolase enzymes are a large class of enzymes that include cholinesterases, hydrolases, lipases, and proteases. In one aspect, the serine hydrolase probe has a fluorophosphonate (FP) group that covalently modifies the active sites of serine hydrolases. Only active serine hydrolases can be modified. The methods and systems of the activity-based HCP profiling of the present application provide the advantages of labelling HCP impurities which have active enzymatic activities, such as active proteases and active lipases. These active proteases and lipases might be problematic for drug integrity in various processing steps.

In some exemplary embodiments, the methods and systems of the activity-based HCP profiling of the present application in combination with mass spectrometry (MS) can be used to identify protein sequences of enzymatic HCP impurities. In one aspect, the methods and systems of the present application in combination with MS can be used to identify active enzymatic HCP impurities. In one aspect, when a fluorescent probe is used as the activity-based probe in the methods and systems of the present application, active enzymatic HCP impurities can be visualized. In another aspect, the methods and systems of the activity-based HCP profiling of the present application can be used to quantitate active enzymatic HCP impurities.

The methods and systems of the present application provide the advantages of direct detection and quantification of enzymatic activities of HCP impurities rather than simply quantitating the abundance of the presence of HCP impurities. The methods and systems of the present application also provide the advantages of monitoring the functional state of large numbers of enzymes in HCP impurities.

The demands of improving the product quality, efficacy and safety of biopharmaceutical products have led to an increasing demand for monitoring HCP impurities which have enzymatic activities. This disclosure provides methods and systems to satisfy the aforementioned demands. Exemplary embodiments disclosed herein satisfy the aforementioned demands by providing methods and systems for identifying, profiling, characterizing, or quantifying HCP impurities which have enzymatic activities in biopharmaceutical products and in samples during manufacturing processes. The present application provides various activity-based probes to characterize different enzyme classes of HCP impurities to satisfy the long felt needs.

The term "a" should be understood to mean "at least one"; and the terms "about" and "approximately" should be understood to permit standard variation as would be understood by those of ordinary skill in the art; and where ranges are provided, endpoints are included. As used herein, the terms "include," "includes," and "including," are meant to be non-limiting and are understood to mean "comprise," "comprises," and "comprising," respectively.

In some exemplary embodiments, the present application provides a system for identifying, profiling, characterizing or quantifying HCP impurities in a sample, the system comprising: at least one probe, wherein the at least one probe comprises a warhead and a tag, wherein the at least one probe is capable of binding to HCP impurities to provide probe-attached HCP impurities, wherein the warhead is capable of binding to an active site of the probe-attached HCP impurity, and wherein the sample comprises at least one high-abundance protein; a solid support; an enzymatic digestion solution capable of generating components of the isolated probe-attached HCP impurities; and a mass spectrometer capable of identifying, profiling, characterizing or quantifying the components from the isolated probe-attached HCP impurity.

As used herein, the term "protein" includes any amino acid polymer having covalently linked amide bonds. Proteins comprise one or more amino acid polymer chains, generally known in the art as "polypeptides". A protein may contain one or multiple polypeptides to form a single functioning biomolecule. In some exemplary embodiments, the protein can be an antibody, a monoclonal antibody, a bispecific antibody, a multi-specific antibody, an antibody fragment, a Fab region of an antibody, an antibody-drug conjugate, a fusion protein, a protein pharmaceutical product, a drug or combinations thereof.

As used herein, a "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

In one aspect, the at least one high-abundance protein in the sample of the method can be an antibody, a bispecific antibody, an antibody fragment, a Fab region of an antibody, an antibody-drug conjugate, a fusion protein, a protein pharmaceutical product or a drug.

As used herein, an "antibody" is intended to refer to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

As used herein, a "protein pharmaceutical product" includes an active ingredient which can be fully or partially biological in nature. In one aspect, the protein pharmaceutical product can comprise a peptide, a protein, a fusion protein, an antibody, an antigen, vaccine, a peptide-drug conjugate, an antibody-drug conjugate, a protein-drug conjugate, cells, tissues, or combinations thereof. In another aspect, the protein pharmaceutical product can comprise a recombinant, engineered, modified, mutated, or truncated version of a peptide, a protein, a fusion protein, an antibody, an antigen, vaccine, a peptide-drug conjugate, an antibody-drug conjugate, a protein-drug conjugate, cells, tissues, or combinations thereof.

In one aspect, the mass spectrometer of the method of the present application can be an electrospray ionization mass spectrometer, nano-electrospray ionization mass spectrometer, such as an Orbitrap mass spectrometer, a Q-TOF mass spectrometer or a triple quadrupole mass spectrometer, wherein the mass spectrometer is coupled to a liquid chromatography system. In one aspect, the mass spectrometer of the method is capable of performing LC-MS (liquid chromatography-mass spectrometry), nano-LC-MS, LC-MS/MS, nano-LC-MS/MS or a LC-MRM-MS (liquid chromatography-multiple reaction monitoring-mass spectrometry) analyses.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus. In some exemplary embodiments, the electrospray ionization mass spectrometer can be a nano-electrospray ionization mass spectrometer.

As used herein, the term "triple quadrupole mass spectrometer" refers to a tandem mass spectrometer consisting of two quadrupole mass analyzers in series, with a (non-mass-resolving) radio frequency (RF)-only quadrupole between them to act as a cell for collision-induced dissociation. In a triple quadrupole mass spectrometer, a peptide sample is injected onto an LC coupled with a MS instrument. The first quadrupole can be used as a mass filter to isolate peptides with a targeted m/z. The second quadrupole serves as a collision cell to break the peptide into fragments. The third quadrupole serves as a second mass filter for specified m/z fragments from the initial parent peptide. As used herein, the term "tandem mass spectrometry" includes a technique where structural information on sample molecules can be obtained by using multiple stages of mass selection and mass separation. A prerequisite is that the sample molecules can be transferred into gas phase and ionized intact and that they can be induced to fall apart in some predictable and controllable fashion after the first mass selection step. Tandem MS have been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometers ions produced in the ion source can be trapped, isolated, fragmented, and m/z separated in the same physical device.

As used herein, the term "liquid chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

Exemplary Embodiments

Embodiments disclosed herein provide methods and systems for identifying, profiling, characterizing or quantifying HCP impurities which have enzymatic activities.

In some exemplary embodiments, the present application provides a method of identifying, profiling, characterizing or quantifying HCP impurities in a sample, the method comprising contacting the sample with at least one probe to provide probe-attached HCP impurities, wherein the probe comprises a warhead and a tag, wherein the warhead is capable of binding to an active site of the probe-attached HCP impurity, and wherein the sample comprises at least one high-abundance protein.

In one aspect, the tag of the probe of the method is a conjugation tag, an affinity tag, or a reporter tag, such as a fluorophore or a fluorophore conjugation site, such as rhodamine, biotin, phosphine, alkyne, azide, acetylene, cyclooctyne, phenyl azide or omega-terminal azide. In one aspect, the warhead of the probe contains fluorophosphonate, epoxysuccinate, photo-activatable lipid, photo-activatable sphingosine, N-acetylated amino acid, quinolimine methide coupled amino acid, or p-aminomandelic acid coupled amino acid. In one aspect, the probe of the method comprises azido-fluorophosphonate; desthiobiotin-fluorophosphonate; tetramethylrhodamine-fluorophosphonate; ethyl (2S,3S)-epoxysuccinate-Leu-Tyr-Acp-Lys(Biotin)-NH$_2$; 1-palmitoyl-2-(9-(3-pent-4-ynyl-3-H-diazirin-3-yl)-nonanoyl)-sn-glycero-3-phosphocholine; (2S,3R,E)-2-amino-13-(3-(pent-4-yn-1-yl)-3H-diazirin-3-yl)tridec-4-ene-1,3-diol; N-(9-(3-pent-4-ynyl-3-H-diazirin-3-yl)-nonanoyl)-D-erythro-sphingosine; 1,2-dipalmitoyl-sn-glycero-3-phosphoethanolamine-N-(5-hexynoyl); or D-galactosyl-β-1,1' N-(6"-azidohexanoyl)-D-erythro-sphingosine. In another aspect, the active site of the probe-attached HCP impurity of the method is a cysteine protease active site, a serine protease active site, a serine hydrolase active site, a cathepsin active site, a metalloprotease active site, a cholinesterase active site, an active site of a lipid-binding protein, an active site of a sphingolipid-binding protein, an active site of a ceramide-binding protein, a lipase active site, a protease active site, a hydrolase active site, an oxidoreductase active site, or an isomerase active site.

It is understood that the system is not limited to any of the aforesaid HCP impurities, activity-based probes, enzymatic active sites, warheads, conjugation tags, affinity tags, reporter tags, solid supports, pharmaceutical products, peptides, proteins, antibodies, anti-drug antibodies, chromatography column, or mass spectrometer.

The consecutive labeling of method steps as provided herein with numbers and/or letters is not meant to limit the method or any embodiments thereof to the particular indicated order. Various publications, including patents, patent applications, published patent applications, accession numbers, technical articles and scholarly articles are cited throughout the specification. Each of these cited references is incorporated herein by reference, in its entirety and for all purposes. Unless described otherwise, all technical and scientific terms used herein have the same meaning as commonly understood by one of ordinary skill in the art to which this invention belongs. This disclosure will be more fully understood by reference to the following Examples, which are provided to describe this disclosure in greater detail. They are intended to illustrate and should not be construed as limiting the scope of this disclosure.

Examples

Material and Reagents
1. Biopharmaceutical Products Containing HCP Impurities

Figure 2:
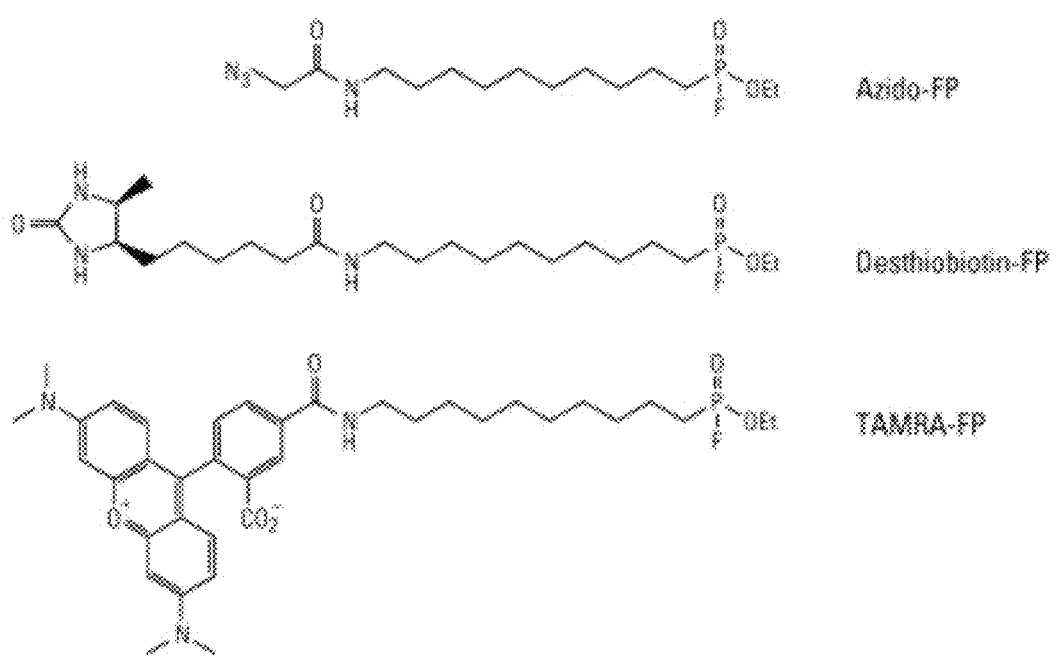
FIG. 2 shows chemical structures of serine hydrolase probes including azido-FP, desthiobiotin-FP and TAMRA-FP according to an exemplary embodiment.

Several biopharmaceutical samples containing HCP impurities, such as samples containing monoclonal antibodies and HCP impurities, were used for characterizing enzymatic HCP impurities. These samples included: (1) clarified cell culture supernatant (5 mg) from CHO cells; (2) LPL (Lipoprotein Lipase) and PLBD2 (Phospholipase B Domain-Containing Protein 2) knockout AEX material (LPL-PLBD2 knockout-AEX, 5 mg) which contained cell culture supernatant from CHO cells derived from LPL-PLBD2 knockout CHO cell line and processed by anion exchange (AEX) chromatography; (3) AEX material (AEX-supernatant, 5 mg) which contained cell culture supernatant processed by anion exchange chromatography; (4) drug substance (DS, 10 mg) which contained purified biopharmaceutical products, such as purified monoclonal antibodies; (5) drug substance which was spiked with lipases at 10 ppm (spiked-DS, 10 mg) including acid ceramidase, PLBD2, lipoprotein lipase, and lysosomal acid lipase.
2. Serine Hydrolase Probes Serine hydrolase probes, e.g., Pierce™ ActivX™ Serine Hydrolase Probes (Thermo Fisher Scientific), were used to label, assay, purify or detect HCP impurities which have serine hydrolase activities as shown in FIG. 1 and FIG. 2. Several serine hydrolase probes containing fluorophosphonate (FP) can be used to modify the serine residue in the active site of serine hydrolases including lipases and proteases, since FP can specifically initiate the covalent modification of the serine nucleophile in the active site. FIG. 1 shows the mechanism and structure of serine hydrolase probes for modifying the active site of serine hydrolases. FIG. 2 shows the chemical structures of serine hydrolase probes including azido-FP, desthiobiotin-FP and TAMRA-FP (tetramethylrhodamine-fluorophosphonate). Azido-FP probes can be used in combination with phosphine- or alkyne-derived tags for detection or enrichment. Desthiobiotin-FP probes can be used for affinity enrichment and detection of serine hydrolases by Western blot or mass spectrometry, such as in combination with streptavidin Dynabeads. TAMRA-FP probe has a fluorescent tag which enables the labelling and detection of serine hydrolase activity in samples through fluorescent gel imaging, capillary electrophoresis or mass spectrometry.

Figure 3:
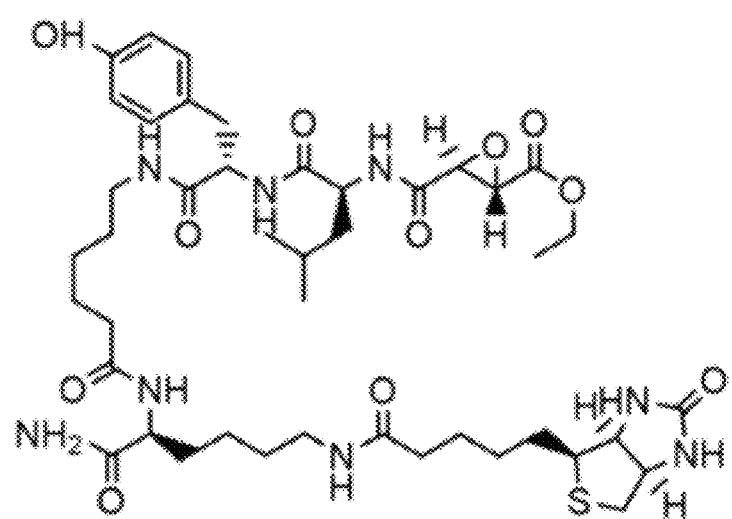
FIG. 3 shows the chemical structure of a cysteine protease probe, DCG-04, e.g., Ethyl (2S,3S)-epoxysuccinate-Leu-Tyr-Acp-Lys(Biotin)-NH$_2$, CD-892 according to an exemplary embodiment.
Figure 4:
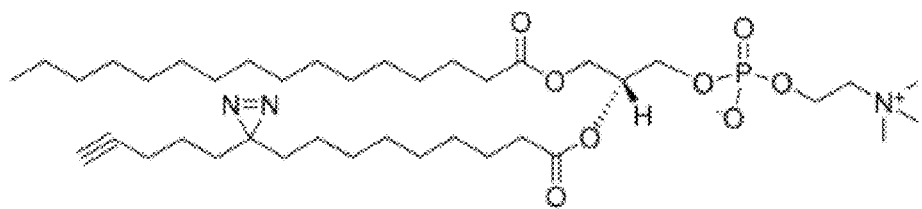
FIG. 4 shows the chemical structure of a lipid probe, 16:0-pacFA PC, e.g., 1-palmitoyl-2-(9-(3-pent-4-ynyl-3-H-diazirin-3-yl)-nonanoyl)-sn-glycero-3-phosphocholine according to an exemplary embodiment.

The workflows for profiling, capturing, and detecting serine hydrolases in HCP samples with ActivX™ FP probes include pre-incubation of samples with probes (e.g., inhibitors) and determination of inhibitor specificity, binding affinity and potency through Western blot, fluorescent SDS-PAGE or mass spectrometry.
3. Cysteine Protease Probe A cysteine protease probe, DCG-04, was used to profile cathepsin activity as shown in FIG. 3. DCG-04, for example, Ethyl (2S,3S)-epoxysuccinate-Leu-Tyr-Acp-Lys(Biotin)-$NH_2$, CD-892, an epoxysuccinate-containing probe for clan CA cysteine proteases, is based on the naturally occurring inhibitor E-64 and targets the papain family of cysteine proteases via covalent attachment of the epoxysuccinate group to the active site cysteine. DCG-04 probe can be used for affinity enrichment and detection of cysteine proteases by Western blot or mass spectrometry, such as in combination with streptavidin Dynabeads.
4. Lipid Probe, 16:0-pacFA PC A lipid probe, 16:0-pacFA PC, e.g., 1-palmitoyl-2-(9-(3-pent-4-ynyl-3-H-diazirin-3-yl)-nonanoyl)-sn-glycero-3-phosphocholine, was used to purify sphingolipid-binding proteins as shown in FIG. 4. This probe provides photo-activatable linkage of lipid to proteins in close proximity. The lipid-labelled protein can be subsequently conjugated to beads using the alkyne moiety through azide-alkyne Huisgen cycloaddition to azide functionalized beads. The lipid-labelled proteins can be enriched or purified through the isolation of the conjugated-beads.
5. Lipid probe, PhotoClick Sphingosine (900600)

Figure 5:
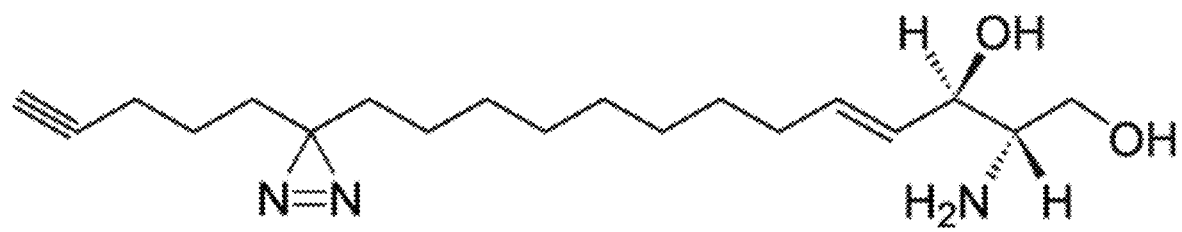
FIG. 5 shows the chemical structure of a lipid probe, PhotoClick Sphingosine (900600), e.g., (2S,3R,E)-2-amino-13-(3-(pent-4-yn-1-yl)-3H-diazirin-3-yl)tridec-4-ene-1,3-diol according to an exemplary embodiment.

A lipid probe, PhotoClick Sphingosine (900600), e.g., (2S,3R,E)-2-amino-13-(3-(pent-4-yn-1-yl)-3H-diazirin-3-yl)tridec-4-ene-1,3-diol, was used to purify sphingosine proteins as shown in FIG. 5. This probe provides photo-activatable linkage of lipid to proteins in close proximity. The lipid-labelled protein can be subsequently conjugated to beads using the alkyne moiety through azide-alkyne Huisgen cycloaddition to azide functionalized beads. The lipid-labelled proteins can be enriched or purified through the isolation of the conjugated-beads. This photo-activatable and clickable analog of sphingosine has been used to profile sphingolipid-binding proteins in sphingosine-1-phosphate lyase deficient cells to understand the global cellular interplay between sphingolipids and their interacting proteins (Haberkant et al., Bifunctional Sphingosine for Cell-Based Analysis of Protein-Sphingolipid Interactions, ACS Chem Biol., 2016, Jan. 15;11(1):222-30. doi: 10.1021/acschembio.5b00810. Epub 2015 Nov. 25).
6. Lipid Probe, pacFA Ceramide (900404)

Figure 6:
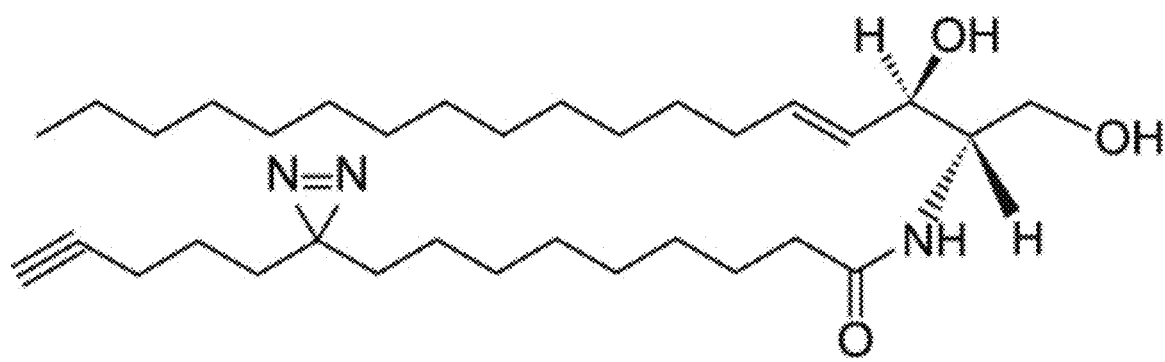
FIG. 6 shows the chemical structure of a lipid probe, pacFA ceramide (900404), e.g., N-(9-(3-pent-4-ynyl-3-H-diazirin-3-yl)-nonanoyl)-D-erythro-sphingosine according to an exemplary embodiment.
Figure 7:
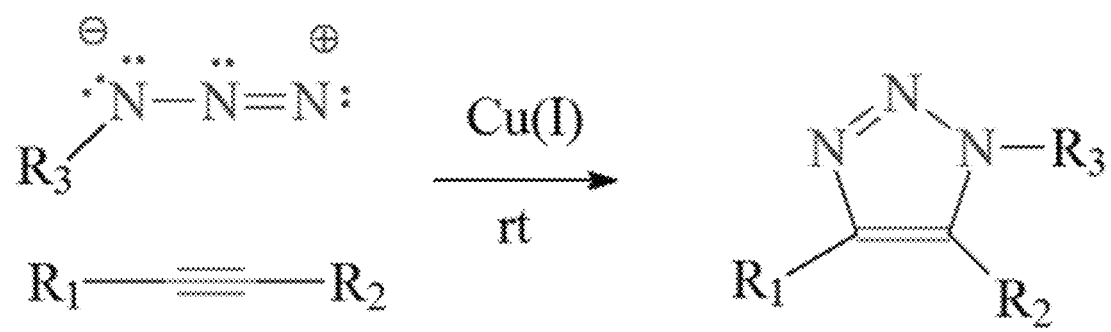
FIG. 7 shows the chemical structures and mechanisms of copper-catalyzed azide-alkyne cycloaddition reaction according to an exemplary embodiment.

A lipid probe, pacFA ceramide (900404), for example, N-(9-(3-pent-4-ynyl-3-H-diazirin-3-yl)-nonanoyl)-D-erythro-sphingosine, was used to purify ceramide-binding proteins as shown in FIG. 6. This probe provides linkage of lipid to proteins in close proximity. The lipid-labelled protein can be subsequently conjugated to beads using the alkyne moiety through azide-alkyne Huisgen cycloaddition to azide functionalized beads. The lipid-labelled proteins can be enriched or purified through the isolation of the conjugated-beads.
7. Agarose and Beads with Azide-Alkyne Cycloaddition Reaction Agarose and magnetic beads were used to pull down the labelled proteins. Magnetic or agarose beads containing azide can be used to capture proteins which were cross-linked to alkyne-containing lipid through copper-catalyzed azide-alkyne cycloaddition reaction. FIG. 7 shows the chemical structures and mechanisms of copper-catalyzed azide-alkyne cycloaddition reaction.

8. Lipid Probe, 16:0 Hexynoyl PE (870127)

Figure 8:
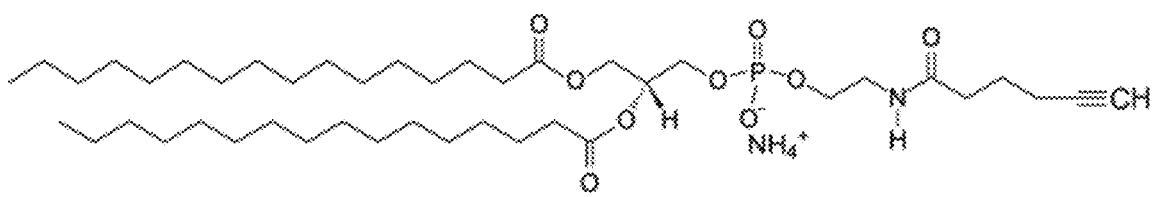
FIG. 8 shows the chemical structure of a lipid probe, 16:0 hexynoyl PE (870127), e.g., 1,2-dipalmitoyl-sn-glycero-3-phosphoethanolamine-N-(5-hexynoyl) (ammonium salt) according to an exemplary embodiment. This probe contains ester linkages similar to those hydrolyzed in PS-20 (polysorbate 20).
Figure 8:
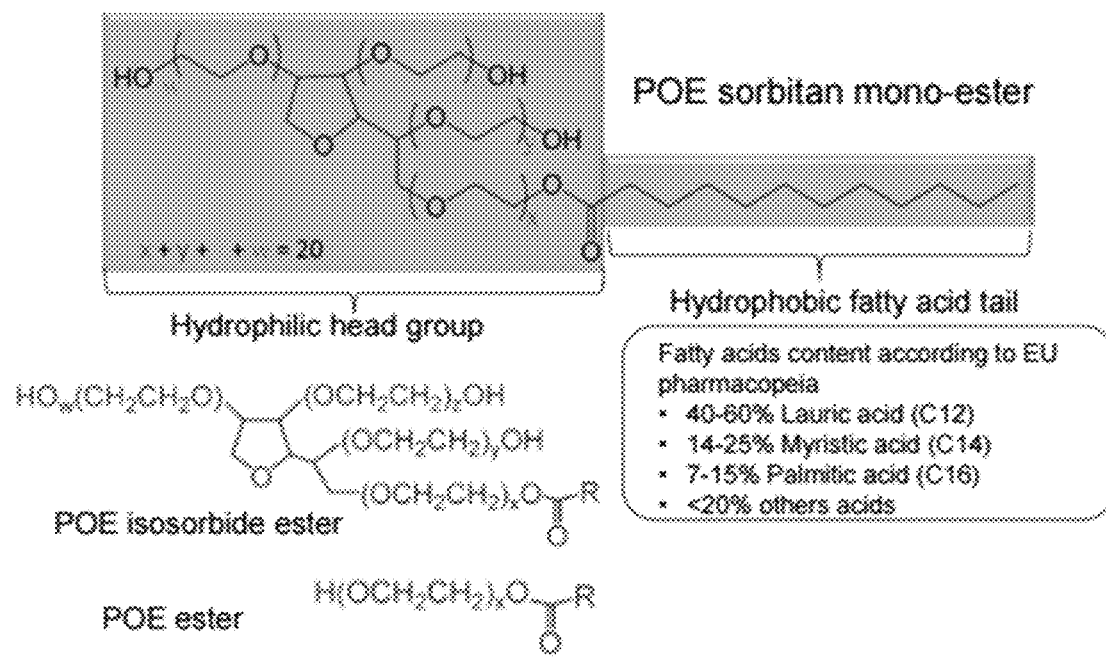

A lipid probe, 16:0 hexynoyl PE (870127), for example, 1,2-dipalmitoyl-sn-glycero-3-phosphoethanolamine-N-(5-hexynoyl) (ammonium salt), was used to purify lipid-binding proteins as shown in FIG. 8. This probe was used to purify labelled proteins using the alkyne moiety through azide-alkyne Huisgen cycloaddition to azide functionalized beads or between cyclooctyne and phenyl azide-functionalized beads. The labelled proteins can be enriched or purified through the isolation of the conjugated-beads. This probe contains ester linkages similar to those hydrolyzed in PS-20 (polysorbate 20). However, the photo-activatable linkage is not available.

9. Lipid Probe, C6(6-Azido) GalCer (860833)

Figure 9:
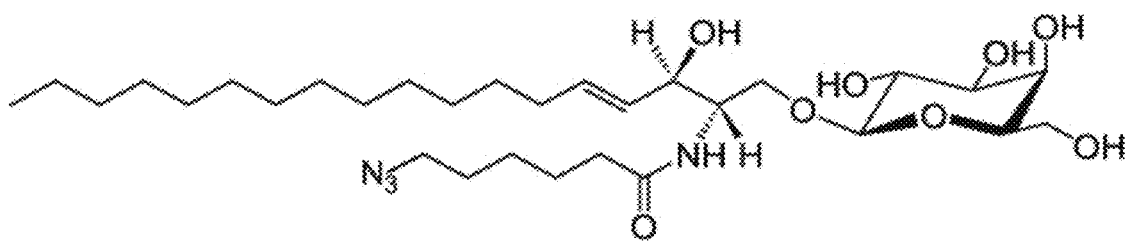
FIG. 9 shows the chemical structure of a lipid probe, C6(6-azido) GalCer (860833), e.g., D-galactosyl-β-1,1' N-(6"-azidohexanoyl)-D-erythro-sphingosine according to an exemplary embodiment.

A lipid probe, C6(6-azido) GalCer (860833), e.g., D-galactosyl-β-1,1' N-(6"-azidohexanoyl)-D-erythro-sphingosine, which is an azide-functionalized sphingolipid with sugar group as shown in FIG. 9, was used to purify lipid-binding proteins. This probe is a modified lipid containing an omega-terminal azide. The terminal azide group can be used in a highly specific linking reaction with alkyne-containing reagents, e.g., click chemistry, in the presence of a copper (Cu)-containing catalyst.

10. Reagent and Sample Preparation for Labelling HCP Impurities with Serine Hydrolase Probes Labelling buffer (10× TBS (Tris buffered saline), $MgCl_2$, $CaCl_2$, NP-40): 500 mM potassium phosphate buffer, pH 7.5, containing 20 mM $MgCl_2$, 5 mM $CaCl_2$ and 1% NP-40. 0.2 g of $MgCl_2$, 0.1 g of $CaCl_2$ and 1 mL of NP-40 added to 100 mL of 10× TBS.

10 M urea lysis buffer: 0.9 g of urea dissolved with 1.5 mL of Lysis Buffer for each labeling reaction.

1.5 M urea in 1× TBS: 1.35 g of urea dissolved with 10 mL 1× TBS.

Lipase mixture: (LPL: Lipoprotein Lipase; LIPA: Lipase A lysosomal acid type; ASAH: N-Acylsphingosine Amidohydrolase, Acid Ceramidase; PLBD2: Phospholipase B Domain Containing 2). 10 ppm lipases were spiked in samples for conducting the experiments.

TABLE 1

Preparation of lipase mixture.

| | Sample Lot | Concentration of lipase | Volume for master mix (mL) | Concentration in master mix | μg to give 10 ppm in 10 mg |
|---|---|---|---|---|---|
| LPL | MAB2-L8 | 0.491 | 10.18 | 0.05 | 0.1 |
| LIPA | MAB3-L1 | 0.7 | 7.14 | 0.05 | 0.1 |
| ASAH | MAB4-L1 | 0.43 | 11.63 | 0.05 | 0.1 |
| PLBD2 | MAB5-L4 | 1.66 | 3.01 | 0.05 | 0.1 |
| PBS buffer | | | 68.03 | | |

500 mM Iodoacetamide: 60 μL of water added to one pre-weighed vial (56 mg) of iodoacetamide.

5 M urea lysis buffer: 1 mL of 10 M Urea/IP Lysis Buffer diluted with 1 mL of Lysis Buffer for each labeling reaction.

50 mM biotin in 1× TBS: 40.9 mL of 1× TBS and 1 mL of ammonium hydroxide added to 500 mg of biotin. Vortex the solution and store it at 4° C.

5 mM biotin in 1× TBS: 900 μL of 1× TBS added to 100 μL of 50 mM biotin.

Digestion buffer containing trypsin: one vial of 20 μg trypsin dissolved in 1000 μL of 5 mM biotin elution buffer. 20 μL of 1 mU/μL PNGase F and 100 μL of 1% protease max added.

11. Reagent and Sample Preparation for Labelling HCP Impurities with Lipid Probes.

10 M urea lysis buffer: 0.9 g of urea dissolved with 1.5 mL of Lysis Buffer for each labeling reaction.

Digestion buffer (2M urea/20 mM Tris, pH 8.0): 2.4 g of urea dissolved with 0.4 mL 1M Tris, pH 8.0 and 19.6 mL of LC-MS grade water.

10 ppm lipases were spiked in samples for conducting the experiments. The lipases included LPL, LIPA, ASAH, and PLBD2. (LPL: Lipoprotein Lipase; LIPA: Lipase A lysosomal acid type; ASAH: N-Acylsphingosine Amidohydrolase, Acid Ceramidase; PLBD2: Phospholipase B Domain Containing 2). The samples, MAB1-C3-DS, contained monoclonal antibody (MAB1) and HCP impurities.

Buffer S (PBS, 1% SDS): 1 mL of 10% SDS added to 9 mL of PBS and vortexed to mix.

500 mM DTT: 7.7 mg of DTT dissolved with 0.1 mL water.

1 M Iodoacetamide: 18.4 mg of iodoacetamide dissolved with 0.1 mL water.

16:0-pacFA PC solution (molecular weight: 741.978 g/mol): 674 μL ethanol added to 16:0-pacFA PC to make a 2 mM stock solution.

Methods

1. Label, Enrich and Identify HCP Impurities with Serine Hydrolase Probes:

Samples containing HCP impurities were labelled with serine hydrolase probes, such as desthiobiotin-FP. Subsequently, labelled HCP impurities were enriched and identified. Samples containing HCP impurities were prepared according to Table 2 for labelling HCP impurities with serine hydrolase probes. Lysate samples were diluted with lysis buffer and transferred to a micro-centrifuge tube according to Table 2. CCF in Table 2 indicates cell culture fluid, e.g., supernatant sample, clarified cell culture supernatant sample or clarified cell culture fluid sample. AEX in Table 2 indicates anion exchange chromatography. DS in Table 2 indicates drug substance. Standards in Table 2 indicates the mixture of recombinant lipase proteins as shown in Table 1. "LPL and PLBD2 KO AEX Pool Material" indicates cell culture material collected from cells from a LPL (Lipoprotein Lipase)-PLBD2 (Phospholipase B Domain-Containing Protein 2) double knockout CHO cell line. Conc. indicates concentration.

TABLE 2

Sample preparations for labelling HCP impurities with serine hydrolase probes.

| | Conc. (mg/mL) | Sample (μL) | Labeling Buffer (μL) | Lipases (μL) | Water (μL) | Sample (mg) | Final Volume (mL) | Probe (μL) |
|---|---|---|---|---|---|---|---|---|
| Bioreactor Fluid | 27.4 | 182.5 | 100 | 0 | 217.5 | 5 | 0.5 | 20 |
| AEX Pool | 14.8 | 337.8 | 100 | 0 | 62.2 | 5 | 0.5 | 20 |
| DS | 214 | 46.7 | 100 | 0 | 353.3 | 10 | 0.5 | 20 |
| DS Plus Standards | 214 | 46.7 | 100 | 2 | 351.3 | 10 | 0.5 | 20 |
| LPL and PLBD2 KO AEX Pool Material | 5.6 | 892.9 | 200 | 0 | 0.0 | 5 | 1 | 20 |
| Bioreactor Fluid (no probe) | 27.4 | 182.5 | 100 | 0 | 217.5 | 5 | 0.5 | 0 |

The serine hydrolase probe containing fluorophosphonate (FP), serine hydrolase FP probe, was equilibrated to room temperature in a pouch with desiccants. Subsequently, serine hydrolase FP probe was dissolved in 100 μL DMSO to make a 0.1 mM stock solution. The stock solution of serine hydrolase FP probe was added to each sample to reach a final mix concentration of 4 μM. The samples were incubated for 60 minutes at room temperature.

The samples were filtered using micro-biospin 6 desalting columns or equivalent to remove unbound probes, including the steps of: (1) invert the column sharply several times to re-suspend the settled gel and remove any bubbles; snap off the tip and place the column in a 2.0 mL micro-centrifuge tube; remove the top cap; if the column does not begin to flow, push the cap back on the column and then remove it again to start the flow; allow the excess packing buffer to drain by gravity to the top of the gel bed (about two minutes); discard the drained buffer then place the column back into the 2.0 mL tube; (2) centrifuge for 2 minutes in a micro-centrifuge at 1,000 xg to remove the remaining packing buffer; discard the buffer; (3) apply 500 μL of 5 M Urea/Lysis Buffer; after each application of new buffer, let the buffer drain out by gravity, or centrifuge the column for 1 minute to remove the buffer; discard buffer from collection tube; repeat 3 times; (4) place the column in a clean 1.5 or 2.0 mL micro-centrifuge tube; carefully apply the sample (20-75 μl) directly to the center of the column (application of more or less than the recommended sample volume may decrease column performance); (5) after loading the sample, centrifuge the column for 4 minutes at 1,000 xg; and (6) following centrifugation, the purified sample is in 5 M urea buffer.

The labelled HCP impurities were captured, digested and analyzed including the steps of: (1) add 500 μL of 5 M urea/Lysis Buffer to each reaction for a total volume of 1 mL; (2) add 2 mg of streptavidin dynabeads (purchased from Thermo Fisher Scientific) to each sample to capture labelled HCP impurities and incubate for 1 hour at room temperature with constant mixing on a rotator; (3) collect dynabeads using a magnetic rack for 3 minutes; remove supernatant; (4) add 500 μL of 5 M urea/Lysis Buffer and vortex briefly to mix; collect beads using a magnet and remove the supernatant; repeat this step two additional times; discard buffer after each wash; (5) add 1.5 M urea solution with 5 mM TCEP and incubate at 55° C. for 30 minutes; (6) add iodoacetamide to a final concentration of 10 mM and shake the beads in the dark at room temperature for 30 minutes; (7) wash once with 1000 μL 1× TBS; (8) for eluting labelled HCP impurities, add 75 μL 5 mM biotin elution solution and shake for 10 minutes at 37° C., then collect the supernatant; (9) add trypsin elution solution to the beads and shake for 10 minutes at 37° C., then combine the supernatant with the previous elution step; (10) digest overnight at 37° C.; (11) add 4 μL of 20% TFA, vortex and incubate at room temperature for 10 minutes; (12) centrifuge for 5 minutes at 14,000 xg; and (13) load 18 μL treated eluted labeled HCP impurities on the nano-LC and analyze by nano-LC-MS/MS.

2. Label, Enrich and Identify HCP Impurities with Lipid Probes:

Samples containing HCP impurities were labelled with lipid probes, such as 16:0-pacFA PC. Subsequently, labelled HCP impurities were enriched and identified. Samples containing HCP impurities were prepared according to Table 3 for labelling HCP impurities with lipid probes. Lysate samples were diluted with PBS (phosphate buffer saline) and transferred to a micro-centrifuge tube according to Table 3. AEX in Table 3 indicates anion exchange chromatography. DS in Table 3 indicates drug substance. MAB1-DS indicates drug substance containing monoclonal antibody, MAB1. Standards in Table 3 indicates the mixture of recombinant lipase proteins as shown in Table 1. "LPL and PLBD2 KO AEX Pool Material" indicates cell culture material collected from cells from a LPL (Lipoprotein Lipase)-PLBD2 (Phospholipase B Domain-Containing Protein 2) double knockout CHO cell line.

TABLE 3

Sample preparations for labelling HCP impurities with 16:0-pacFA PC.

| | Conc. (mg/mL) | Sample (μL) | Labeling Buffer (μL) | Lipases (μL) | Sample (mg) | Final Volume (mL) | Probe (μL) |
|---|---|---|---|---|---|---|---|
| Bioreactor Fluid | 15 | 166.7 | 100 | 0 | 5 | 0.5 | 10 |
| Bioreactor Fluid (no UV control) | 15 | 166.7 | 100 | 0 | 5 | 0.5 | 10 |
| AEX Pool | 14.8 | 337.8 | 100 | 0 | 5 | 0.5 | 10 |
| DS | 214 | 46.7 | 100 | 0 | 10 | 0.5 | 10 |
| MAB1-DS Plus Standards | 214 | 46.7 | 100 | 2 | 10 | 0.5 | 10 |
| LPL and PLBD2 KO AEX Pool Material | 5.6 | 892.9 | 200 | 0 | 5 | 1 | 20 |
| AEX Pool (no probe) | 14.8 | 337.8 | 100 | 0 | 5 | 0.5 | 0 |

The lipid probe, 16:0-pacFA PC, was equilibrated to room temperature in a pouch. Subsequently, the lipid probe was dissolved in 674 μL ethanol to make a 2 mM stock solution. The unused probe can be stored in glass vial for up to 6 months at −80° C. 10 μL of 16:0-pacFA PC stock solution was added to each sample for a final mix concentration of 20 μM. The reaction mixtures were protected from light, when the photo-activatable probe was added. The sample was incubated for 60 minutes at room temperature. The samples were exposed to greater than 345 nm UV light from a UV trans-illuminator at 365 nm for 15 min at a distance of 5 cm from the light source on ice.

The labelled HCP impurities were captured, digested and analyzed. Subsequently unreacted lipid probe was removed by TCA (trichloroacetic acid) precipitation. Cell lysate, ice-cold acetone, and TCA solution (100% TCA, w/v) were mixed in a 1:8:1 ratio, such as mixing 1 mL cell lysate, 8 mL 100% ice-cold acetone and 1 mL 100% TCA. TCA precipitation was performed at −20° C. for 1 hr followed by centrifugation at 11,500 rpm (18,000 xg) for 15 min at 4° C. in a micro-centrifuge. Supernatant was discarded. Precipitated pellets were washed with 1 mL ice-cold acetone to re-suspend pellets completely followed by centrifugation at 11,500 rpm for 15 min at 4° C. Washing and centrifugation steps were repeated twice to remove all of the TCA. All acetone was removed. The pellet was dried at room temperature to remove residual acetone. The protein pellet was dissolved in 800 μL of buffer S and was transferred to a 1.5 mL eppendorf tube. The protein solution was kept in a shaker at 37° C. for 30 minutes including vortexing approximately every 10 min.

Picolyl azide-agarose resin was prepared by: washing and mixing the picolyl azide-agarose resin in 50% resin slurry for complete re-suspension, transferring 200 μL of the well-mixed resin with a 1 mL pipet into a clean 2 mL centrifuge tube, adding 1.3 mL water, pelleting the resin using centrifugation for 2 minutes at 1000 xg, and aspirating the supernatant by leaving approximately 200 μL of the resin. A catalyst solution was prepared by: using 4730 μL water, 550 μL Additive 1, 110 μL of Copper (II) sulfate solution and 110 μL Additive 2 to prepare 5.5 mL of 2× copper catalyst solution for enrichment. A sample mixture was prepared for conjugating the labelled HCP impurities to agarose resin (beads) by combining 200 μL washed picolyl azide-agarose resin, 800 μL sample and 1000 μL of 2× copper solution. The sample solution was rotated for mixing overnight.

The agarose wash buffer containing SDS was warmed up to room temperature. The resin was centrifuged. Subsequently, the supernatant was aspirated. 1.8 mL water was added to the resin. Subsequently, the resin was centrifuged. Subsequently, the supernatant was aspirated. 1 mL agarose wash buffer containing SDS and 10 μL of 1 M DTT were added to the resin to re-suspend the resin. The resin was heated at 70° C. on a heating block for 15 minutes, followed by cooling to room temperature for 15 minutes. Subsequently the resin was centrifuged for 5 minutes at 1000 xg. The supernatant was aspirated. 6 mL of 40 mM iodoacetamide was prepared by dissolving 44.4 mg of iodoacetamide in 6 mL of agarose wash buffer containing SDS. 1 mL of 40 mM iodoacetamide was added to the resin followed by vortexing the resin for re-suspending. Subsequently, the resin was incubated in the dark for 30 minutes at room temperature. The resin was re-suspended and transferred to a spin column. 2 mL of wash buffer containing SDS was added to the spin column followed by centrifuging at 1000 xg for 1 minute with three repeating processes. 2 mL of 8 M urea/100 mM Tris pH 8 was added to the spin column followed by centrifuging at 1000 xg for 1 minute with five repeating processes. 2 mL of 20% acetonitrile was added to the spin column followed by centrifuging at 1000 xg for 1 min with five repeating processes. A cap was added to the bottom of the spin column followed by adding 500 μL of digestion buffer (100 mM Tris, 2 mM $CaCl_2$, 10% acetonitrile). A 1 mL pipet was used to transfer the resin to a new tube. The spin column was rinsed with another 500 μL of digestion buffer by combining the resin in the new tube. 20 μL of 0.1 μg/μL trypsin and protease max was added to the samples (final concentration of protease max=0.05%). 2 μL of 1 mU/μL PNGase F was added, followed by incubating with rotation overnight. The resin was pelleted by centrifuging for 5 min at 1000 xg. The supernatant was retained. 500 μL of water was added to wash the beads two times. All of the supernatants were combined. 2 μL of TFA was added. The digestion mixture was desalted and concentrated using a C-18 cartridge. The eluent was dried down from desalted sample and analyzed by nano-LC-MS/MS.

3. Label, Enrich and Identify HCP Impurities with Cysteine Protease Probes:

Samples containing HCP impurities were labelled using cysteine protease probes, such as DCG-04. Subsequently, labelled HCP impurities were enriched and identified. Samples containing HCP impurities were prepared according to Table 4 for labelling HCP impurities with cysteine protease probes. The 10× reaction buffer contained 500 mM sodium acetate (pH 6), 10 mM EDTA, and 25 mM DTT.

The cysteine protease probe, DCG-04, was equilibrated to room temperature in a pouch. Subsequently, the probe was dissolved in 2000 μL DMSO to make a 0.5 mM stock solution. 5 μL of DCG-04 stock solution was added to each sample for a final mix concentration of 2.5 μM. The samples were incubated for 60 minutes at room temperature.

The samples were filtered using Amicon 3 kDa molecular weight desalting filters to remove unbound probes, including the steps of: (1) apply each sample to the top of the desalting filters; (2) apply 500 μL of 8 M guanidine to the top of each filter; (3) apply 500 μL of 5 M Urea/Lysis Buffer to the top of the filter; (4) at the end of each step centrifuge at 14,000 xg for 20 minutes, then discard the volume from the collection tube. Finally, place the column in a clean collection tube, invert the filter and centrifuge for 2 minutes at 2,000 xg to collect the buffer-exchanged and labelled samples.

The labelled HCP impurities were captured, digested and analyzed including the steps of: (1) add 500 μL of 5 M urea/Lysis Buffer to each reaction; (2) add 1 mg of streptavidin dynabeads (purchased from Thermo Fisher Scientific) to each sample to capture labelled HCP impurities and incubate for 1 hour at room temperature with constant mixing on a rotator; (3) collect dynabeads using a magnetic rack for 3 minutes; remove supernatant; (4) add 500 μL of 5 M urea/Lysis Buffer and vortex briefly to mix; collect beads using a magnet and remove the supernatant; repeat this step two additional times; discard buffer after each wash; (5) add 1.5 M urea solution with 5 mM TCEP and incubate at 55° C. for 30 minutes; (6) add iodoacetamide to a final concentration of 10 mM and shake the beads in the dark at room temperature for 30 minutes; (7) wash once with 1000 μL 1× TBS; (8) add trypsin elution solution to the beads and shake for 4 hours at 37° C. to completely digest and elute proteins from the beads; (10) add 4 μL of 20% TFA, vortex and incubate at room temperature for 10 minutes; (11) move the supernatant from the beads containing the digested HCP into a clean tube; (12) centrifuge for 5 minutes at 14,000 xg; and (13) load 18 μL treated eluted labeled HCP impurities on the nano-LC and analyze by nano-LC-MS/MS.

TABLE 4

Sample preparations for labelling HCP impurities with cysteine protease probes.

| Sample Name | Concentration (mg/mL) | Volume Sample (μL) | Volume 10× reaction buffer (μL) | Volume 10× HCP standards (μL) | Volume MilliQ water | Amount of sample (mg) | Final volume (mL) | Volume probe (μL) |
|---|---|---|---|---|---|---|---|---|
| MAB2-DS + HCP (no probe) | 221.4 | 45 | 100 | 5.3 | 850 | 10 | 1 | 0 |
| MAB2-DS + spiked HCP | 221.4 | 45 | 100 | 5.3 | 845 | 10 | 1 | 5 |

TABLE 4-continued

Sample preparations for labelling HCP impurities with cysteine protease probes.

| Sample Name | Concentration (mg/mL) | Volume Sample (µL) | Volume 10× reaction buffer (µL) | Volume 10× HCP standards (µL) | Volume MilliQ water | Amount of sample (mg) | Final volume (mL) | Volume probe (µL) |
|---|---|---|---|---|---|---|---|---|
| MAB2-DS | 221.4 | 45 | 100 | 0 | 850 | 10 | 1 | 5 |
| Spiked HCP | NA | NA | 100 | 5.3 | 890 | NA | 1 | 5 |

4. Direct Digestion of Starting Material

Four volumes of ice-cold acetone were added to each sample and precipitated for 1 hour in a −20° C. freezer followed by washing once with ice-cold 80% acetone. Acetone was carefully decanted and dried for 2 minutes on a paper towel. Samples were re-suspended in 20 µL urea denaturing and reducing solution followed by shaking at 800 rpm at 56° C. on the thermomixer for 30 minutes and cooling to room temperature. 6 µL of 50 mM iodoacetamide was added followed by vortexing briefly. The mixture was kept at room temperature in the dark for 30 minutes. Sequencing grade modified trypsin (20 ug/vial) was prepared in 1.95 mL of 50 mM Tris, pH 7.5 to give a final concentration of 10 ng/µL. 100 µL of 100 ng/µL of trypsin and 4.5 µL of protease max were added to the samples (final concentration of protease max=0.05%). 2 µL of 1 mU/µL PNGase F were added. The samples were vortexed for 3-5 seconds, followed by spinning down the sample(s). The final volume of the solution was 125 uL. The final concentration of urea was 1.25 M. The HCP samples were incubated for 5 hours at 37° C. in the dark with shaking at 750 rpm in a thermomixer. The digestion mixtures were acidified with 5 µL of glacial acetic acid followed by vortexing the samples for 3-5 seconds. Subsequently, the samples were centrifuged at 14,000×g for 5 minutes. The pH of the samples was below pH 3. 15 µL of each sample was loaded onto a mass spectrometer and analyzed using the data dependent method (150 minutes, top 20).

Example 1. Enrichment of HCP Impurities Having Serine Hydrolase Activity

A serine hydrolase probe, desthiobiotin-FP, was used to enrich, identify, characterize or profile HCP impurities which had serine hydrolase activities. Several samples containing biopharmaceutical products, such as monoclonal antibodies, and HCP impurities from CHO cells were used for the enrichments. These samples included clarified-supernatant, LPL-PLBD2 knockout-AEX (designated as AEX KO in Table 5), AEX-supernatant (designated as AEX in Table 5), DS and spiked-DS (designated as DS+lipase in Table 5). The experiments were conducted by incubating samples with desthiobiotin-FP at a final probe concentration of 4 µM for 1 hour at room temperature. Excess probes were removed by buffer exchanges. Some samples were used as controls for monitoring non-specific binding in the absence of desthiobiotin-FP during incubation. For protein enrichments, HCP impurities which were labeled with desthiobiotin-FP were captured using magnetic beads, such as streptavidin-beads. Subsequently, the beads were washed using stringent 5 M urea. Labelled HCPs were eluted using 5 mM biotin. The eluted labelled HCPs were digested overnight at 37° C. and subsequently loaded directly onto nano-LC (liquid chromatography) using trap. Protein identifications were conducted using nano-LC-MS/MS. The experimental results are shown in Table 5. MAB1 HC indicates the heavy chain of monoclonal antibody MAB1. MAB1 LC indicates the light chain of monoclonal antibody MAB1,

TABLE 5

Identifications of HCP impurities.

| Protein Name | Protein Activity/Function | AEX | AEX KO | DS | DS + Lipase |
|---|---|---|---|---|---|
| MAB1 HC | | High | High | High | High |
| MAB1 LC | | High | High | High | High |
| ScFV | Non-CHO protein fusion of HC and LC | High | High | High | High |
| Protein unc-93-like B1 | Protein transport | High | High | High | High |
| Complement C1r-A subcomponent | Serine protease, complement system | High | Not Found | High | Not Found |
| Lipoprotein lipase | Serine hydrolase, lipase | Not Found | Not Found | Not Found | High |
| Histone H2A type 1 | Histone | Peak Found | Peak Found | Peak Found | High |
| Annexin | Lipid binding protein | High | High | High | High |
| Peroxisome proliferator-activated receptor delta | Fatty acid binding protein | High | High | High | High |
| Elongation factor 1-alpha | Protein transport | High | Peak Found | High | Peak Found |

TABLE 5-continued

Identifications of HCP impurities.

| Protein Name | Protein Activity/Function | AEX | AEX KO | DS | DS + Lipase |
|---|---|---|---|---|---|
| Histone H3.1t | Histone | Not Found | Not Found | Not Found | High |
| Maltase-glucoamylase, intestinal-like protein | Alpha-glucosidase | High | High | High | High |
| Actin, cytoplasmic 1 | Structural protein | Not Found | High | High | Peak Found |
| Calcium-dependent serine proteinase | Serine protease | High | Not Found | Not Found | Not Found |
| Putative phospholipase B-like 2 | Serine hydrolase, lipase | High | Not Found | Not Found | Not Found |
| Sucrase-isomaltase, intestinal-like protein | Alpha-glucosidase | Not Found | High | High | High |
| Putative inactive serine protease 58-like protein | Serine protease (similar to trypsin) | High | High | High | High |
| Glyceraldehyde-3-phosphate dehydrogenase | Glycolysis enzyme | High | Peak Found | High | Peak Found |
| Peroxiredoxin-1 | Hydrogen peroxide reduction | High | Peak Found | Peak Found | Not Found |
| Peptidyl-prolyl cis-trans isomerase | Proline isomerase, protein binding | Peak Found | Not Found | Peak Found | High |
| L-lactate dehydrogenase | Lactate to pyruvate conversion | High | Not Found | High | Not Found |
| Serine protease HTRA1 | Serine protease | High | Not Found | Not Found | Not Found |
| Lamin-A/C | Structural protein | Peak Found | High | High | Not Found |
| Peroxiredoxin-2 | Hydrogen peroxide reduction | High | Not Found | High | Not Found |
| Sal-like protein 2 | Nucleic acid binding | Peak Found | Peak Found | High | High |
| Lipase | Serine hydrolase, lipase | Not Found | Not Found | Not Found | High |
| Transient receptor potential cation channel subfamily V member 5 | Structural protein | Not Found | Not Found | High | Not Found |
| Glutathione S-transferase Mu 6 | Catalyzes glutathione addition to substrates with electrophilic groups | Not Found | Not Found | High | Not Found |
| 14-3-3 protein sigma | Protein binding, signaling | Not Found | Peak Found | High | Not Found |
| Annexin | Lipid binding | Not Found | Not Found | High | Peak Found |

Figure 10:
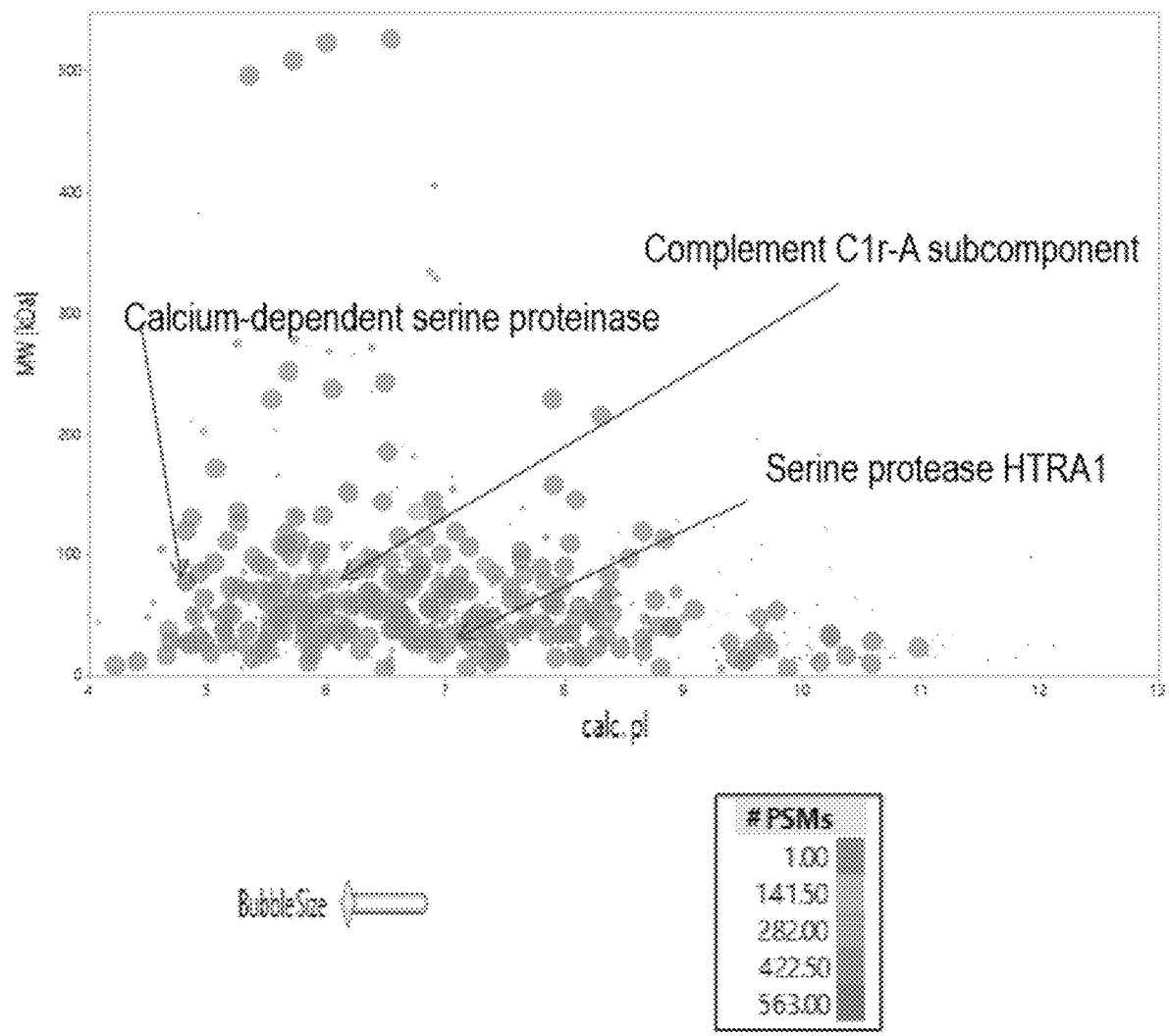
FIG. 10 shows the molecular weights and calculated isoelectric points, e.g., pI, of the 586 proteins which were identified in labelled HCPs in a clarified Chinese Hamster Ovary (CHO) cell-supernatant sample according to an exemplary embodiment. The dot size indicates the differences in protein abundance of labelled HCPs in the clarified-supernatant sample with a probe and without a probe according to an exemplary embodiment. The protein abundance was denoted as color scale from red (high abundance) to blue (low abundance) according to an exemplary embodiment.

Various proteins were identified in HCP impurities in clarified-supernatant samples (e.g., clarified cell culture supernatant sample or cell culture fluid sample). There were 586 proteins identified in eluted labelled HCPs in clarified Chinese Hamster Ovary (CHO) cell-supernatant samples. Within these 586 proteins, 359 proteins were not found in non-specific binding control samples (e.g., in the absence of desthiobiotin-FP during incubation). According to gene ontology analysis, 68% of these 586 proteins had catalytic activities. The molecular weights and calculated isoelectric points (pI) of these 586 proteins were analyzed as shown in FIG. 10. The dot size in FIG. 10 indicates the differences in protein abundance of eluted labelled HCPs in clarified-supernatant samples with a probe and without a probe. The clarified-supernatant sample without a probe was a control for non-specific binding. The protein abundance was denoted as color scale from red (high abundance) to blue (low abundance). Three abundant proteins, e.g., calcium-dependent serine proteinase, complement C1r-A subcomponent, and serine protease HTRA1, were marked as shown in FIG. 10.

Active lipases and esterases which were identified HCP impurities in clarified-supernatant samples after enrichment with the serine hydrolase probe are shown in Table 6. CCF in Table 6 indicates cell culture fluid, for example, clarified-supernatant sample, clarified cell culture supernatant sample or clarified cell culture fluid sample. Calc. pI indicates calculated isoelectric points. PSMs indicates the number of peptide spectrum matches. The number of PSMs is the total number of identified peptide spectra matched for the protein. The PSM value may be higher than the number of peptides identified for high-scoring proteins because peptides may be identified repeatedly. PEP indicates posterior error probability which is the probability that the observed PSM is incorrect. Sum PEP score is calculated on the basis of the PEP values of the PSMs.

TABLE 6

Active lipases and esterases identified in clarified-supernatant sample treated with serine hydrolase probe.

| Accession | Protein Name | Found in CCF | Sum PEP Score | Coverage [%] | # PSMs | MW [kDa] | Calc. pI |
|---|---|---|---|---|---|---|---|
| A0A061IKA1 | Lipoprotein lipase | High | 100.363 | 46 | 39 | 54.5 | 7.85 |
| G3HQY6 | Lipase | High | 89.381 | 39 | 45 | 45.6 | 7.68 |
| G3I6T1 | Putative phospholipase B-like 2 | High | 43.073 | 28 | 22 | 65.5 | 6.28 |
| G3HH63 | Phospholipase A-2-activating protein | High | 2.527 | 2 | 1 | 87.1 | 6.16 |
| G3GZB2 | Acid ceramidase | High | 14.094 | 11 | 6 | 44.7 | 7.9 |
| A0A061I883 | Liver carboxylesterase 22-like protein (Fragment) | High | 7.876 | 16 | 6 | 27.9 | 6.09 |
| G3I7X5 | Liver carboxylesterase 4 | High | 61.579 | 83 | 38 | 11.9 | 5.48 |
| G3IHH9 | Isoamyl acetate-hydrolyzing esterase 1-like | High | 33.533 | 44 | 14 | 31.3 | 5.53 |
| A0A061IFE2 | Liver carboxylesterase 1-like protein | High | 134.525 | 32 | 77 | 97.5 | 6.35 |
| G3IP80 | Acyl-protein thioesterase 2 | High | 13.903 | 37 | 4 | 17.7 | 7.42 |
| G3HNG2 | Acyl-coenzyme A thioesterase 2, mitochondrial (Fragment) | High | 60.516 | 35 | 20 | 49.8 | 8.22 |
| A0A06116Q8 | Liver carboxylesterase B-1-like protein | High | 124.983 | 20 | 66 | 90.2 | 7.34 |
| G3I7X4 | Carboxylic ester hydrolase (Fragment) | High | 16.692 | 14 | 8 | 56.7 | 7.31 |
| G3I5K6 | Carboxylic ester hydrolase | High | 16.206 | 13 | 8 | 56.8 | 6.48 |
| G3I1Y9 | Sulfated glycoprotein 1 | High | 1.173 | 3 | 1 | 27.4 | 5.49 |

Figure 11:
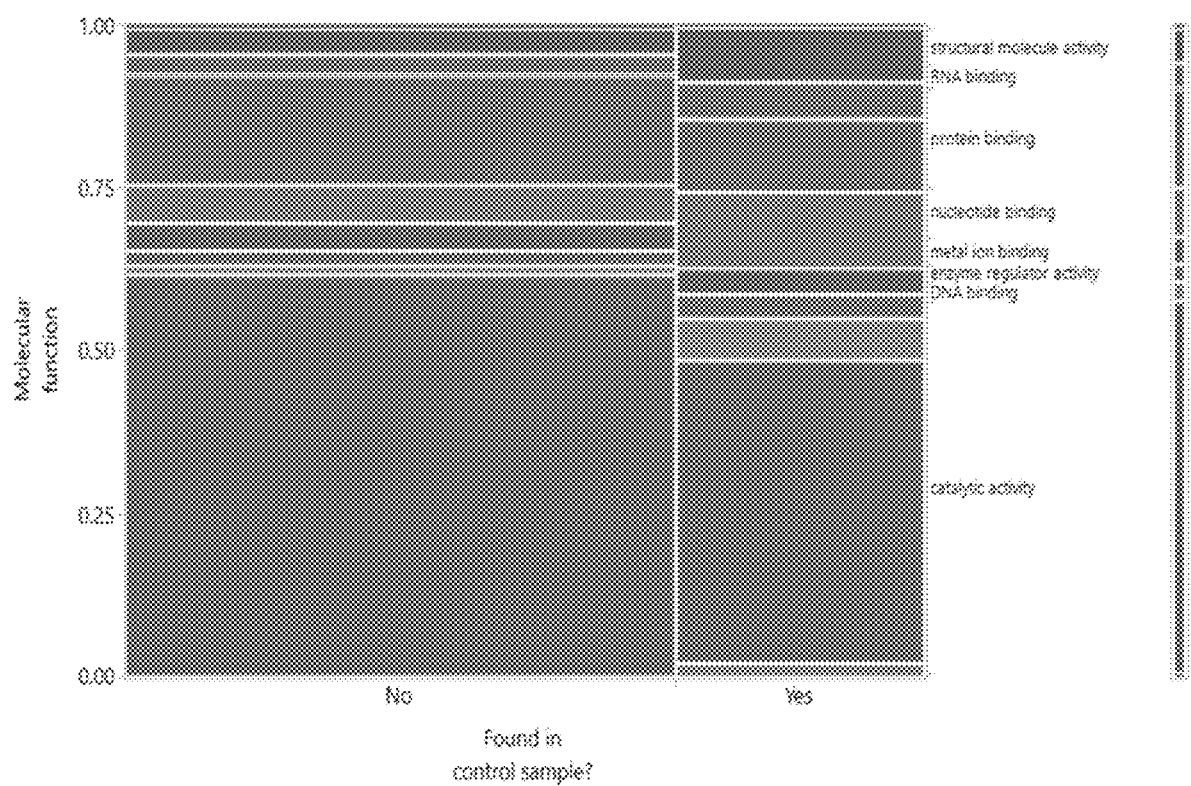
FIG. 11 shows the results of gene ontology analysis for the HCP impurities which were enriched using serine hydrolase probes according to an exemplary embodiment.

There were 586 proteins identified in eluted labelled HCPs in clarified-supernatant samples. Within these 586 proteins, 359 proteins were not found in non-specific binding control samples (e.g., in the absence of desthiobiotin-FP during incubation). The results of gene ontology analysis of these 359 proteins are shown in FIG. 11. The results indicated that the HCP impurity proteins having catalytic activities were significantly enriched using serine hydrolase probe, e.g., desthiobiotin-FP, in comparison with control samples.

Example 2. Enrichment of HCP Impurities Having Lipid-Binding Activities

Many hydrophobic proteins, such as lipases, can bind to fatty acids in cells. Fatty acid-based probes, such as a clickable lipid probe, were used to enrich, identify, characterize or profile hydrophobic HCP impurities, such as lipases or proteins having lipid-binding activities, for example, lipid binding protein. These lipid probes were tested for activity-based profiling of HCP impurities. In addition, these lipid probes were tested for identifying HCP impurities which can bind to polysorbate-like molecules in the cell culture supernatant or in process samples.

A lipid probe, 16:0-pacFA PC, e.g., 1-palmitoyl-2-(9-(3-pent-4-ynyl-3-H-diazirin-3-yl)-nonanoyl)-sn-glycero-3-phosphocholine, was used to purify sphingolipid-binding HCP impurities. This probe had a photo-activatable diazirine ring that can react with proteins in close proximity when it is exposed to UV light. This probe also contained an alkyne for click-chemistry based purification. The lipid-labelled HCP impurities were subsequently conjugated to beads using the alkyne moiety through azide-alkyne Huisgen cycloaddition to azide functionalized beads. The lipid-labelled HCP impurities were subsequently enriched or purified through the isolation of the conjugated-beads.

Figure 12:
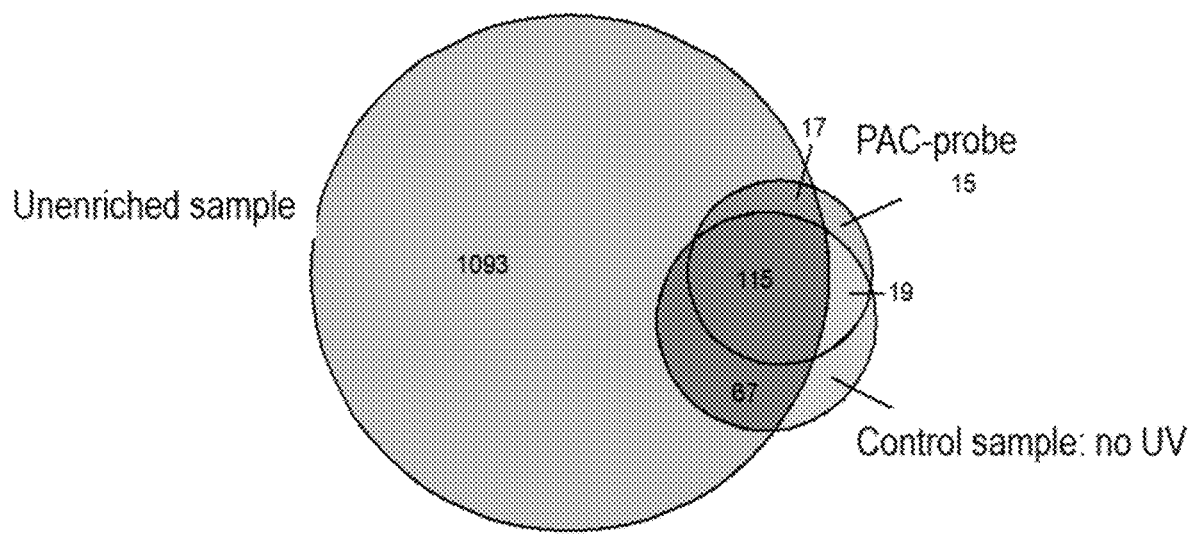
FIG. 12 shows the comparisons of identified HCP impurities among an unenriched sample, a sample enriched by 16:0-pacFA PC probe, and a control sample (no UV) according to an exemplary embodiment.

The HCP impurities in the cell supernatant sample which were specifically enriched using 16:0-pacFA PC included malate dehydrogenase (fragment), beta-galactosidase (fragment), glutathione synthetase, insulin-like growth factor-binding protein 4, leukocyte elastase inhibitor A, prostaglandin reductase 1-like protein, cysteine-rich with EGF-like domain protein 2, pigment epithelium-derived factor, bleomycin hydrolase, citrate synthase, angiopoietin-related protein 4, N-acetylglucosamine-1-phosphotransferase subunit gamma, proteasome subunit beta type-1, 40S ribosomal protein S28, cysteine and glycine-rich protein 1, tripeptidyl-peptidase 1, and splicing factor (proline- and glutamine-rich). Among these identified HCP impurities, beta-galactosidase, insulin-like growth factor-binding protein 4, prostaglandin reductase 1-like protein and angiopoietin-related protein 4 were considered to have potential sphingolipid binding based on the literature. The comparisons of identified HCP impurities among unenriched sample, sample enriched by 16:0-pacFA PC probe, and control sample (no UV) are shown in FIG. 12.

The lipid probe, 16:0-pacFA PC, was used to enrich proteins in DS (drug substance) sample containing spiked recombinant lipases. The specifically enriched proteins included vomeronasal type-2 receptor 26, centriolin, NFX1-type zinc finger-containing protein 1, desmoglein-4-like protein, glyceraldehyde-3-phosphate dehydrogenase, tubulin alpha chain, acid ceramidase, putative non-specific cytotoxic cell receptor protein 1 like protein (fragment), putative inactive serine protease 58-like protein, fatty acid-binding protein (adipocyte), histone acetyltransferase, proteasome endopeptidase complex (fragment), proteasome subunit alpha type, and putative phospholipase B-like 2. Among these identified proteins, acid ceramidase and putative phospholipase B-like 2 were spiked recombinant lipase proteins.

Example 3. Enrichment of Proteins with Cysteine Protease Activity

A cysteine protease probe, DCG-04, was used to enrich proteins in the DS sample containing a spiked recombinant host cell protein mixture (HCP mix) at 100 ppm. The mixture consisted of three cysteine proteases (Cathepsin L1, Cathepsin Z, Cathepsin B) and two other commonly detected host cell proteins that should not have any cysteine protease activity (Beta-hexosaminidase and Cathepsin D). All the spiked recombinant host cell proteins were identified in the sample incubated with the probe, but not in a sample without the probe added, as shown in Table 7. The peak area for the top 3 peptides from each identified protein was averaged and then divided by the peak areas for the top 3 peptides from trypsin to normalize protein abundances across samples. Two of the recombinant cysteine proteases (Cathepsin Z and Cathepsin B) were enriched to levels ~11 fold higher than the other spiked recombinant proteins.

TABLE 7

Active proteases identified in DS sample spiked with a mixture of host cell proteins and treated with cysteine protease probe.

| Protein Description | Protein Accession | DS w/ HCP mix (no probe) | DS w/ HCP mix | DS | HCP mix |
|---|---|---|---|---|---|
| Beta-hexosaminidase | G3HXN7 | 0.004 | 0.011 | 0.000 | 0.087 |
| Cathepsin D | G3I4W7 | 0.000 | 0.003 | 0.000 | 0.014 |
| Cathepsin B | G3HOL9 | 0.000 | 0.102 | 0.001 | 0.236 |
| Cathepsin L1 | G3INC5 | 0.000 | 0.004 | 0.000 | 0.143 |
| Cathepsin Z | Q9EPP7 | 0.000 | 0.058 | 0.005 | 0.142 |
| Trypsin | TRYP_PIG | 1 | 1 | 1 | 1 |

What is claimed:

1. A method of identifying host cell protein (HCP) impurities in a sample containing at least one high-abundance protein, the method comprising:
   contacting the sample with at least one probe capable of attaching to a HCP impurity, wherein the probe includes a warhead and a tag, and wherein the warhead is capable of binding to an active site of the probe-attached HCP impurity;
   contacting the sample with a solid support, wherein the solid support comprises a ligand, and wherein the ligand is capable of binding to the tag; and
   washing the solid support using a solution to provide an eluent to isolate the probe-attached HCP impurity.

2. The method of claim 1, wherein the warhead is capable of binding covalently to a residue in the active site of the probe-attached HCP impurity.

3. The method of claim 1, wherein the tag is a conjugation tag, an affinity tag, or a reporter tag.

4. The method of claim 1 further comprising:
   treating the eluent with an enzymatic digestion reaction to generate components of the isolated probe-attached HCP impurity; and
   subsequently identifying the components of the isolated probe-attached HCP impurity using a mass spectrometer.

5. The method of claim 1, wherein the warhead comprises an enzymatic inhibitor, an enzymatic substrate-based scaffold or a protein-reactive molecule.

6. The method of claim 1, wherein the at least one probe further comprises a linker.

7. The method of claim 1, wherein the at least one high-abundance protein is an antibody, a bispecific antibody, an antibody fragment, a Fab region of an antibody, an antibody-drug conjugate, a fusion protein, a protein pharmaceutical product, or a drug.

8. The method of claim 4, wherein an enzyme of the enzymatic digestion reaction is trypsin.

9. The method of claim 4, wherein the mass spectrometer is an electrospray ionization mass spectrometer, nano-electrospray ionization mass spectrometer, a Q-TOF mass spectrometer or a triple quadrupole mass spectrometer, wherein the mass spectrometer is coupled to a liquid chromatography system.

10. The method of claim 4, wherein the mass spectrometer is capable of performing LC-MS (liquid chromatography-mass spectrometry), nano-LC-MS, LC-MS/MS, nano-LC-MS/MS or a LC-MRM-MS (liquid chromatography-multiple reaction monitoring-mass spectrometry) analyses.

11. The method of claim 1, wherein the tag is detected using Western blot, capillary electrophoresis, SDS-PAGE, fluorescent visualization, or fluorescent gel imaging.

12. The method of claim 1, wherein the active site of the probe-attached HCP impurity is a cysteine protease active site, a serine protease active site, a serine hydrolase active site, a cathepsin active site, a metalloprotease active site, a cholinesterase active site, an active site of a lipid-binding protein, an active site of a sphingolipid-binding protein, an active site of a ceramide-binding protein, a lipase active site, a protease active site, a hydrolase active site, an oxidoreductase active site, or an isomerase active site.

13. The method of claim 1, wherein the tag comprises a fluorophore or a fluorophore conjugation site comprising rhodamine, biotin, phosphine, alkyne, azide, acetylene, cyclooctyne, phenyl azide, or omega-terminal azide.

14. The method of claim 1, wherein the warhead comprises fluorophosphonate, epoxysuccinate, photo-activatable lipid, photo-activatable sphingosine, N-acetylated amino acid, quinolimine methide coupled amino acid, or p-aminomandelic acid coupled amino acid.

15. The method of claim 1, wherein the probe comprises azido-fluorophosphonate; desthiobiotin-fluorophosphonate; tetramethylrhodamine-fluorophosphonate; ethyl (2S,3S)-epoxysuccinate-Leu-Tyr-Acp-Lys(Biotin)-NH$_2$; 1-palmitoyl-2-(9-(3-pent-4-ynyl-3-H-diazirin-3-yl)-nonanoyl)-sn-glycero-3-phosphocholine; (2S,3R,E)-2-amino-13-(3-(pent-4-yn-1-yl)-3H-diazirin-3-yl)tridec-4-ene-1,3-diol; N-(9-(3-pent-4-ynyl-3-H-diazirin-3-yl)-nonanoyl)-D-erythro-sphingosine; 1,2-dipalmitoyl-sn-glycero-3-phosphoethanolamine-N-(5-hexynoyl); or D-galactosyl-β-1,1' N-(6"-azidohexanoyl)-D-erythro-sphingosine.

16. A system for identifying host cell protein (HCP) impurities in a sample, comprising:
- at least one probe, wherein the at least one probe comprises a warhead and a tag, wherein the at least one probe is capable of binding to a HCP impurity to provide a probe-attached HCP impurity, wherein the warhead is capable of binding to an active site of the probe-attached HCP impurity, and wherein the sample comprises at least one high-abundance protein;
- a solid support, wherein the solid support comprises a ligand which is capable of binding to the tag;
- a solution for washing the solid support to provide an eluent to isolate the probe-attached HCP impurity;
- an enzymatic digestion solution capable of generating components of the isolated probe-attached HCP impurity; and
- a mass spectrometer capable of identifying the components from the isolated probe-attached HCP impurity.

17. The system of claim 16, wherein the warhead is capable of binding covalently to a residue in the active site of the probe-attached HCP impurity.

18. The system of claim 16, wherein the tag is a conjugation tag, an affinity tag, or a reporter tag.

19. The system of claim 16, wherein the warhead comprises an enzymatic inhibitor, an enzymatic substrate-based scaffold or a protein-reactive molecule.

20. The system of claim 16, wherein the at least one probe further comprises a linker.

21. The system of claim 16, wherein the at least one high-abundance protein is an antibody, a bispecific antibody, an antibody fragment, a Fab region of an antibody, an antibody-drug conjugate, a fusion protein, a protein pharmaceutical product, or a drug.

22. The system of claim 16, wherein an enzyme of the enzymatic digestion solution is trypsin.

23. The system of claim 16, wherein the mass spectrometer is an electrospray ionization mass spectrometer, nano-electrospray ionization mass spectrometer, a Q-TOF mass spectrometer or a triple quadrupole mass spectrometer, wherein the mass spectrometer is coupled to a liquid chromatography system.

24. The system of claim 16, wherein the mass spectrometer is capable of performing LC-MS (liquid chromatography-mass spectrometry), nano-LC-MS, LC-MS/MS, nano-LC-MS/MS or a LC-MRM-MS (liquid chromatography-multiple reaction monitoring-mass spectrometry) analyses.

25. The system of claim 16, wherein the tag is detected using Western blot, capillary electrophoresis, SDS-PAGE, fluorescent visualization, or fluorescent gel imaging.

26. The system of claim 16, wherein the active site of the probe-attached HCP impurity is a cysteine protease active site, a serine protease active site, a serine hydrolase active site, a cathepsin active site, a metalloprotease active site, a cholinesterase active site, an active site of a lipid-binding protein, an active site of a sphingolipid-binding protein, an active site of a ceramide-binding protein, a lipase active site, a protease active site, a hydrolase active site, an oxidoreductase active site, or an isomerase active site.

27. The system of claim 16, wherein the tag comprises a fluorophore or a fluorophore conjugation site comprising rhodamine, biotin, phosphine, alkyne, azide, acetylene, cyclooctyne, phenyl azide, or omega-terminal azide.

28. The system of claim 16, wherein the warhead comprises fluorophosphonate, epoxysuccinate, photo-activatable lipid, photo-activatable sphingosine, N-acetylated amino acid, quinolimine methide coupled amino acid, or p-aminomandelic acid coupled amino acid.

29. The system of claim 16, wherein the probe comprises azido-fluorophosphonate; desthiobiotin-fluorophosphonate; tetramethylrhodamine-fluorophosphonate; ethyl (2S,3S)-epoxysuccinate-Leu-Tyr-Acp-Lys(Biotin)-NH$_2$; 1-palmitoyl-2-(9-(3-pent-4-ynyl-3-H-diazirin-3-yl)-nonanoyl)-sn-glycero-3-phosphocholine; (2S,3R,E)-2-amino-13-(3-(pent-4-yn-1-yl)-3H-diazirin-3-yl)tridec-4-ene-1,3-diol; N-(9-(3-pent-4-ynyl-3-H-diazirin-3-yl)-nonanoyl)-D-erythro-sphingosine; 1,2-dipalmitoyl-sn-glycero-3-phosphoethanolamine-N-(5-hexynoyl); or D-galactosyl-β-1,1' N-(6"-azido-hexanoyl)-D-erythro-sphingosine.

\* \* \* \* \*